US009895137B2

(12) United States Patent
Tabaru et al.

(10) Patent No.: US 9,895,137 B2
(45) Date of Patent: Feb. 20, 2018

(54) ULTRASONIC DIAGNOSIS DEVICE AND TRANSMISSION/RECEPTION METHOD

(71) Applicant: HITACHI, LTD., Tokyo (JP)

(72) Inventors: Marie Tabaru, Tokyo (JP); Hideki Yoshikawa, Tokyo (JP); Rei Asami, Tokyo (JP); Kunio Hashiba, Tokyo (JP); Hiroshi Masuzawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 14/413,174

(22) PCT Filed: Jan. 29, 2014

(86) PCT No.: PCT/JP2014/051950
§ 371 (c)(1),
(2) Date: Jan. 6, 2015

(87) PCT Pub. No.: WO2014/136502
PCT Pub. Date: Sep. 12, 2014

(65) Prior Publication Data

US 2015/0173718 A1 Jun. 25, 2015

(30) Foreign Application Priority Data

Mar. 5, 2013 (JP) ................. 2013-042991

(51) Int. Cl.
*A61B 8/00* (2006.01)
*A61B 8/08* (2006.01)
*G01S 7/52* (2006.01)

(52) U.S. Cl.
CPC ............ *A61B 8/485* (2013.01); *A61B 8/08* (2013.01); *A61B 8/085* (2013.01); *A61B 8/463* (2013.01);

(Continued)

(58) Field of Classification Search
CPC ..................................................... A61B 8/08
See application file for complete search history.

(56) References Cited

U.S. PATENT DOCUMENTS 5,999,486 A * 12/1999 DeVault ................ G01V 1/284
367/36
6,023,977 A * 2/2000 Langdon ............... G01N 29/06
367/87

(Continued)

FOREIGN PATENT DOCUMENTS

| JP | 6-319736 A | 11/1994 |
|---|---|---|
| JP | 2012-100997 A | 5/2012 |

(Continued)

OTHER PUBLICATIONS

International Search Report from International Application No. PCT/JP14/051950 dated Mar. 11, 2014.

(Continued)

*Primary Examiner* — Rochelle Turchen
*Assistant Examiner* — Joanne Hoffman
(74) *Attorney, Agent, or Firm* — Brundidge & Stanger, P.C.

(57) ABSTRACT

There is provided an ultrasonic diagnostic apparatus capable of measuring hardness information of a subject with high time resolution and spatial resolution.

The apparatus is provided with a ultrasonic probe 1 and a displacement generation unit 10 configured to displace an inside of a subject and is configured to transmit an ultrasonic beam for displacement detection to a plurality of detection positions of the subject from the ultrasonic probe 1, and to detect a shear wave velocity based on the displacement at the plurality of detection positions in a control unit 3 by using a reflection signal detected in a detection unit 20, thereby outputting hardness information of the subject. The ultrasonic beam for displacement detection is transmitted to one (Continued)

of the plurality of detection positions. A waveform analysis unit 26 of the control unit 3 is configured to perform a change control of analyzing a shear wave resulting from the displacement to thus transmit the ultrasonic beam for displacement detection to another position of the plurality of detection positions. Thereby, it is possible to measure the shear wave velocity with high time resolution and spatial resolution, so that it is possible to obtain the hardness information of the subject with high precision.

20 Claims, 22 Drawing Sheets

(52) U.S. Cl.
CPC .......... *A61B 8/5207* (2013.01); *A61B 8/5223* (2013.01); *G01S 7/52042* (2013.01)

(56) References Cited

U.S. PATENT DOCUMENTS

| | | | |
|---|---|---|---|
| 8,852,102 | B2 | 10/2014 | Miyachi |
| 9,439,620 | B2 | 9/2016 | Tabaru et al. |
| 2005/0004463 | A1* | 1/2005 | Chen ............... A61B 8/08 600/442 |
| 2006/0173319 | A1* | 8/2006 | Sumi ............... A61B 8/08 600/437 |
| 2009/0216119 | A1 | 8/2009 | Fan et al. |
| 2010/0016718 | A1 | 1/2010 | Fan et al. |
| 2010/0069751 | A1 | 3/2010 | Hazard et al. |
| 2010/0220901 | A1 | 9/2010 | Matsumura |
| 2010/0280373 | A1* | 11/2010 | Fan ............... A61B 8/0833 600/439 |
| 2011/0028838 | A1 | 2/2011 | Pernot et al. |
| 2011/0066030 | A1* | 3/2011 | Yao ............... A61B 8/0833 600/438 |
| 2011/0184287 | A1* | 7/2011 | McAleavey ......... A61B 8/4483 600/438 |
| 2011/0216311 | A1* | 9/2011 | Kachanov .......... G01N 21/1702 356/213 |
| 2012/0123263 | A1* | 5/2012 | Osaka ............... A61B 5/0048 600/438 |
| 2012/0136250 | A1* | 5/2012 | Tabaru ............... A61B 8/08 600/438 |
| 2012/0215101 | A1* | 8/2012 | Maleke ............. A61B 5/055 600/438 |
| 2012/0232387 | A1 | 9/2012 | Miyachi |
| 2013/0131511 | A1 | 5/2013 | Peterson et al. |
| 2013/0289402 | A1 | 10/2013 | Tabaru et al. |
| 2014/0221833 | A1* | 8/2014 | Oikawa ............. A61B 8/485 600/438 |

FOREIGN PATENT DOCUMENTS

| | | |
|---|---|---|
| JP | 2012-170823 A | 9/2012 |
| JP | 2012-183261 A | 9/2012 |
| JP | 2013-500752 A | 1/2013 |
| WO | 2007/83745 A1 | 7/2007 |
| WO | WO 2011004661 A1 * | 1/2011 ........... A61B 5/0048 |
| WO | WO 2011027644 A1 * | 3/2011 ............... A61B 8/08 |
| WO | 2011/064688 A1 | 6/2011 |
| WO | 2012077579 A1 | 6/2012 |

OTHER PUBLICATIONS

Jeremy J. Dahl et al., "A Parallel Tracking Method for Acoustic Radiation Force Impulse Imaging", IEEE transaction on ultrasonics, ferroelectrics, and frequency control, vol. 54, No. 2, 2007, pp. 301-312.

Shigao Chen, et al "Quantifying Elasticity and Viscosity from Measurement of Shear Wave Speed Dispersion", The Journal of the Acoustical Society of America, American Institute of Physics for the Acoustical Society of America, New York, NY vol. 115, No. 6, Jun. 1, 2004, pp. 2781-2785.

Thomas Deffieux, et al "On the Effects of Reflected Waves in Transient Shear Wave Elastography", IEEE Transactions on Ultrasonics, Ferroelectrics and Frequency Control, IEEE, US, vol. 58, No. 10, Oct. 1, 2011, pp. 2032-2035.

Extended European Search Report (EESR), dated Oct. 14, 2016.

* cited by examiner

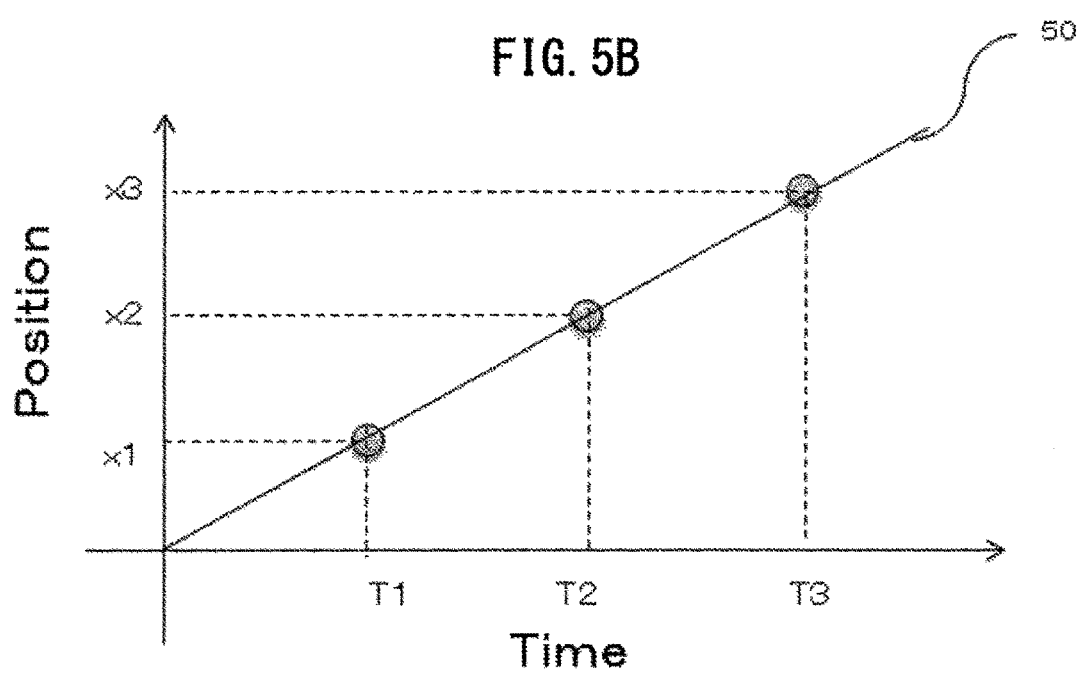

- - - - - - - detection line of shear wave

---------- detection line of shear wave

ULTRASONIC DIAGNOSIS DEVICE AND TRANSMISSION/RECEPTION METHOD

TECHNICAL FIELD

The present invention relates to an ultrasonic diagnostic apparatus, and more particularly, to an ultrasonic technology of transmitting and receiving an ultrasonic wave to detect a shear wave in a subject.

BACKGROUND ART

As a method of diagnosing breast cancer, cirrhosis, vascular disease and the like, there has been known a method (an elastography technology) of diagnosing hardness in a subject such as a living body from an ultrasonic echo signal, instead of palpation of a doctor. When diagnosing the hardness of the subject by the elastography technology, an engaged person touches and presses an ultrasonic probe to a surface of the subject, thereby generating a displacement in a tissue in the subject. Before and after compression of the internal tissue by the pressing, an ultrasonic beam for displacement detection is irradiated to acquire an echo signal, a displacement in the compression direction is estimated on the basis of the acquired echo signal and a distortion, which is a spatial differentiating amount of the displacement, is calculated. Further, a value relating to the hardness, for example, a Young's modulus is calculated from the distortion and stress. Also, as disclosed in NPL 1, there is an elastography technology of using a focused beam of ultrasonic waves to apply a radiation pressure into a subject, displacing a target tissue while suppressing an influence of an interposed layer, irradiating an ultrasonic beam for displacement detection to acquire an echo signal, and diagnosing hardness of the subject such as a living body on the basis of the acquired echo signal.

CITATION LIST

Non-Patent Literature

[NPL 1] Jeremy J. Dahl et al., "A Parallel Tracking Method for Acoustic Radiation Force Impulse Imaging", IEEE transactions on ultrasonics, ferroelectrics, and frequency control, Vol. 54, No. 2, 2007, pp. 301-312.

SUMMARY OF INVENTION

According to the method of touching and pressing the ultrasonic probe to the surface of the subject, a target to be imaged is limited to an organ that can be easily pressed from a body surface. For example, since a slip surface, which is an interposed layer, exists between the body surface and the liver, it is difficult to perform the pressing causing a sufficient displacement in the liver.

According to the method of using the focused beam of ultrasonic waves to apply the radiation pressure into the subject, since the tissue is displaced by the ultrasonic waves, it is possible to reduce an influence of the interposed layer such as the slip surface, which reduces the dependency on the procedure.

In any method, the pressing or radiation pressure is applied to generate a shear wave in the subject, the displacement of the tissue in the subject, which is accompanied by propagation of the shear wave, is detected by the ultrasonic wave for displacement detection and a velocity of the shear wave and the like are estimated to estimate the hardness of the subject and the like. The estimation precision of the shear wave velocity is increased as the number of detection positions of the shear wave by the ultrasonic wave for displacement detection increases. Therefore, a method (a parallel tracking method) of repeating an operation of irradiating an ultrasonic beam pulse for displacement detection in parallel in a time-division manner to a plurality of detection positions so as to detect the displacement at the plurality of detection positions has been known. However, according to this method, a time resolution of the shear wave measurement at the entire measurement positions is limited by PRT (Pulse Repetition Time) of the ultrasonic beam for displacement detection. That is, as the number of the detection positions, to which the ultrasonic beam for displacement detection is irradiated in parallel in the time-division manner, is increased, a period (a time interval) for which the ultrasonic beam for displacement detection is irradiated to the same detection position is prolonged and the time resolution per one position is lowered. Like this, there is a tradeoff relation between the spatial resolution improvement due to the increase in the detection position and the time resolution of the peak position detection of the shear wave.

NPL 1 also discloses a method of enlarging a beam diameter of the ultrasonic beam for detecting the shear wave, irradiating the ultrasonic wave to one place and generating reception waveforms at a plurality of positions from a reception waveform of the irradiated ultrasonic wave, so as to detect the shear waves at the plurality of detection positions at the same time without lowering the time resolution by using the parallel tracking technology. In this case, it is possible to maintain the time resolution. However, since the beam diameter is enlarged, the spatial resolution is lowered.

An object of the present invention is to solve the above problems occurring in the elastography technology and to provide an ultrasonic diagnostic apparatus capable of measuring a shear wave velocity with high time resolution and spatial resolution, and a method of transmitting and receiving an ultrasonic beam.

In order to realize the above object, according to the present invention, there is provided an ultrasonic diagnostic apparatus including a ultrasonic probe; a displacement generation unit configured to displace an inside of a subject and to thus generate a shear wave; a detection unit configured to sequentially transmit a first ultrasonic beam to a plurality of detection positions of the subject from the ultrasonic probe, to receive reflection signals and to detect the displacement at the detection positions by using the received reflection signals, thereby detecting the shear wave, and a control unit configured to calculate a velocity of the shear wave on the basis of an output of the detection unit, thereby outputting hardness information of the subject.

Also, in order to realize the above object, according to the present invention, there is provided a method of transmitting and receiving an ultrasonic beam. The method includes displacing an inside of a subject; transmitting a first ultrasonic beam to one of a plurality of detection positions of the subject from a ultrasonic probe and receiving a reflection signal, and switching the detection position on the basis of the received reflection signal and detecting a shear wave velocity caused due to the displacement at the plurality of detection positions, thereby calculating hardness information of the subject.

According to the present invention, it is possible to measure the shear wave with the high time resolution and spatial resolution.

BRIEF DESCRIPTION OF DRAWINGS

FIG. 5B is a graph showing a relation between time at which the displacement of the shear wave peaks and the detection position in the first illustrative embodiment.

DESCRIPTION OF EMBODIMENTS

Hereinafter, a variety of illustrative embodiments of the present invention will be described with reference to the drawings. First, a configuration example of an ultrasonic diagnostic apparatus that is common to the first through third illustrative embodiments is described. The ultrasonic diagnostic apparatus of the illustrative embodiments is configured to generate a shear wave in a subject tissue, to detect displacement of the subject tissue caused by propagation of the shear wave at a plurality of detection positions and to estimate a shear wave velocity, for example. The shear wave velocity is calculated and estimated by a linear approximation of the detection position and arrival time of the shear wave. Also, the arrival time of the shear wave is estimated by detecting a peak value of a temporal waveform of the shear wave, for example.

Figure 1:
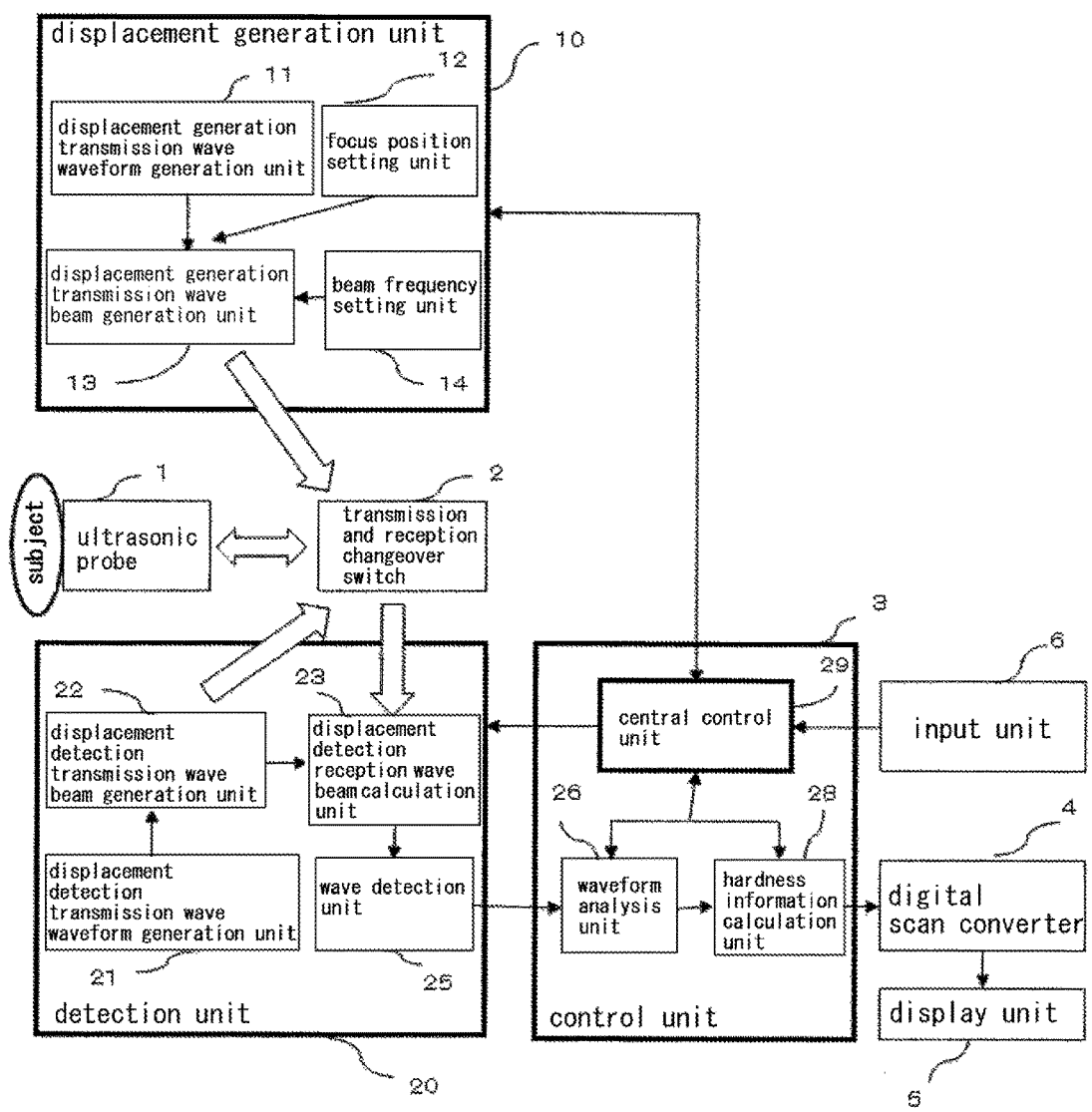
FIG. 1 is a block diagram showing an example of a system configuration of an ultrasonic diagnostic apparatus according to a first illustrative embodiment.

FIG. 1 shows an overall configuration of an example of the ultrasonic diagnostic apparatus according to the first to third illustrative embodiments. The ultrasonic diagnostic apparatus is provided with an ultrasonic probe 1 configured to transmit and receive an ultrasonic beam to and from a subject such as a living body, a transmission and reception changeover switch 2 connected to the ultrasonic probe 1, a displacement generation unit 10 configured to generate a displacement in the subject, a detection unit 20 configured to detect the displacement generated in the subject and a control unit 3 configured to control the displacement generation unit 10 and the detection unit 20. Also, the ultrasonic diagnostic apparatus is further provided with a digital scan converter 4 to which an output of the detection unit 20 is input, a display unit 5 configured to display the output, and an input unit 6 connected to the control unit 3 and configured to perform a variety of inputs, which will be described later. The displacement generation unit 10 includes a displacement generation transmission wave waveform generation unit 11, a focus position setting unit 12, a displacement generation transmission wave beam generation unit 13 and a beam frequency setting unit 14, as described later. The detection unit 20 includes a displacement detection transmission wave waveform generation unit 21, a displacement detection transmission wave beam generation unit 22, a displacement detection reception wave beam calculation unit 23 and a wave detection unit 25. Meanwhile, in the specification, an ultrasonic beam for displacement detection may be also referred to as a first ultrasonic beam and an ultrasonic beam for displacement generation may be also referred to as a second ultrasonic beam.

The control unit 3 includes a waveform analysis unit 26 configured to receive an output of the wave detection unit 25 and to analyze a waveform thereof and a hardness information calculation unit 28 configured to receive an output of the waveform analysis unit 26 and to calculate hardness information of the subject. Also, the control unit 3 includes a central control unit 29 configured to control the waveform analysis unit 26, the hardness information calculation unit 28, the displacement generation unit 10 and the detection unit 20. The ultrasonic probe 1 is connected to the displacement generation transmission wave beam generation unit 13, the displacement detection transmission wave beam generation unit 22 and the displacement detection reception wave beam calculation unit 23 through the transmission and reception changeover switch 2. In FIG. 1, an outline arrow indicates above noted connection relations between the ultrasonic probe 1, the displacement generation transmission wave beam generation unit 13, the displacement detection transmission wave beam generation unit 22, the displacement detection reception wave beam calculation unit 23 and the transmission and reception changeover switch 2.

First, the displacement generation unit 10 of the ultrasonic diagnostic apparatus of FIG. 1 is described. The displacement generation transmission wave beam generation unit 13 in the displacement generation unit 10 is configured to generate a transmission wave signal for each element of the ultrasonic probe 1 having delay time or weighting applied thereto so that an ultrasonic beam is focused on a position set by the focus position setting unit 12, by using the waveform generated in the displacement generation transmission wave waveform generation unit 11, under control of the central control unit 29. The transmission wave signal from the displacement generation transmission wave beam generation unit 13 is converted into an ultrasonic signal at the ultrasonic probe 1, which is then irradiated to the subject such as the living body. Thereby, the second ultrasonic beam, which is the ultrasonic beam for displacement generation, is irradiated. The irradiation starting time and ending time of the ultrasonic beam for displacement generation are set at the beam frequency setting unit 14. Here, a beam frequency indicates a repetition frequency of the irradiation of the ultrasonic beam for displacement generation.

Hereafter, the detection unit 20 of FIG. 1 is described. After the ultrasonic beam for displacement generation is irradiated on the basis of an electric signal (the transmission wave signal) from the displacement generation transmission wave beam generation unit 13, an ultrasonic beam for displacement detection, which is the first ultrasonic beam for detecting a displacement of a tissue in the subject, is irradiated from the ultrasonic probe 1. Like the displacement generation transmission wave beam generation unit 13, the displacement detection transmission wave beam generation unit 22 is configured to generate a transmission wave signal for each element of the ultrasonic probe 1 having delay time or weighting applied thereto so that an ultrasonic beam for displacement detection is focused on a desired position, by using the waveform generated in the displacement detection transmission wave waveform generation unit 21, under control of the central control unit 29.

An echo signal, which is a reflection signal reflected in the subject and returned to the ultrasonic probe 1, is converted into an electric signal at the ultrasonic probe 1, which is then sent to the displacement detection reception wave beam calculation unit 23 via the transmission and reception changeover switch 2. An output of the displacement detection reception wave beam calculation unit 23 is output to the waveform analysis unit 26 in the control unit 3, as a signal indicating a change of the subject tissue resulting from propagation of the shear wave, after signal processing in the wave detection unit 25 such as envelope detection, log compression, bandpass filter processing, gain control and the like. The waveform analysis unit 26 is configured to calculate a displacement of the subject tissue caused due to the shear wave and to analyze the shear wave, based on the input signal. Regarding the analysis of the shear wave, a calculation of detecting a peak value of a temporal waveform of the shear wave and calculating peak time is performed, for example.

An output of the waveform analysis unit 26 is sent to the displacement detection transmission wave beam generation unit 22 via the central control unit 29 and is used to set a detection position and detection time of the shear wave. That is, in the ultrasonic diagnostic apparatus of this illustrative embodiment, the control is performed to switch a detection position of a plurality of detection positions, to which the ultrasonic beam for displacement detection (the first ultrasonic beam) is irradiated, based on the output of the detection unit 20. Also, the detection time at the plurality of detection positions is controlled, based on the output of the detection unit 20.

Also, the detection position and an analysis result are sent to the hardness information calculation unit 28, as an output signal of the waveform analysis unit 26. The analysis result is a signal indicating time at which the displacement of the subject tissue caused due to the shear wave peaks, for example. The hardness information calculation unit 28 is configured to calculate and output a shear wave velocity, a Young's modulus and the like indicating hardness information of the subject tissue, from the input signal. The signal indicating the hardness information, which is output from the hardness information calculation unit 28, is converted into an image signal at the digital scan converter 4, which is then displayed on the display unit 5, as a numerical value or image indicating the hardness information.

In the meantime, for example, a general computer including a central processing unit (CPU), a memory configured to store therein a program and data, and the like executes the program with the CPU, so that the central control unit 29, the waveform analysis unit 26, the hardness information calculation unit 28 and the like, which are parts of the block shown in FIG. 1, can be implemented. The program is stored in the memory and the like of the computer configuration. Alternatively, at least one of the waveform analysis unit 26 and the hardness information calculation unit 28 can be configured by dedicated hardware.

First Illustrative Embodiment

A first illustrative embodiment is an illustrative embodiment of the ultrasonic diagnostic apparatus capable of switching the detection time at a plurality of detection positions for measuring the shear wave in the subject to thus calculate a velocity of the shear wave, thereby estimating the hardness information of the subject. Meanwhile, in the below descriptions, an example where the velocity of the shear wave is calculated as the hardness information of the subject is described. However, the present invention is not limited thereto. That is, the other hardness information such as Young's modulus may be also used in the present invention.

As shown in FIG. 1, the ultrasonic diagnostic apparatus of this illustrative embodiment is provided with the ultrasonic probe 1, the displacement generation unit 10 configured to displace an inside of a subject, the detection unit 20 configured to sequentially transmit a first ultrasonic beam to a plurality of detection positions of the subject from the ultrasonic probe 1, to receive the reflection signals, to detect the displacement of the subject tissue at the detection positions by using the received reflection signals and to thus detect propagation of a shear wave, and the control unit 3 configured to calculate a shear wave velocity on the basis of an output of the detection unit 20 and to output the shear wave velocity as the hardness information of the subject. Also, a method of transmitting and receiving an ultrasonic beam of this illustrative embodiment is an illustrative embodiment of a method of transmitting and receiving an ultrasonic beam including displacing an inside of a subject, transmitting a first ultrasonic beam to one of a plurality of detection positions of the subject from an ultrasonic probe to thus receive an echo signal (a reflection signal), and switching the detection position and detecting a shear wave velocity caused due to the displacement at the plurality of detection positions to thus calculate hardness information of the subject on the basis of the received reflection signal.

The displacement generation unit 10 is configured to emit the ultrasonic beam for displacement generation, which is the second ultrasonic beam, and to thus displace the subject tissue, thereby generating the shear wave, before irradiating the first ultrasonic beam (ultrasonic beam for displacement detection). The detection position and detection time at which the first ultrasonic beam is irradiated so as to detect the shear wave by the detection unit 20 are changed by switching transmission time of the first ultrasonic beam to each of the plurality of detection positions.

Figure 2:
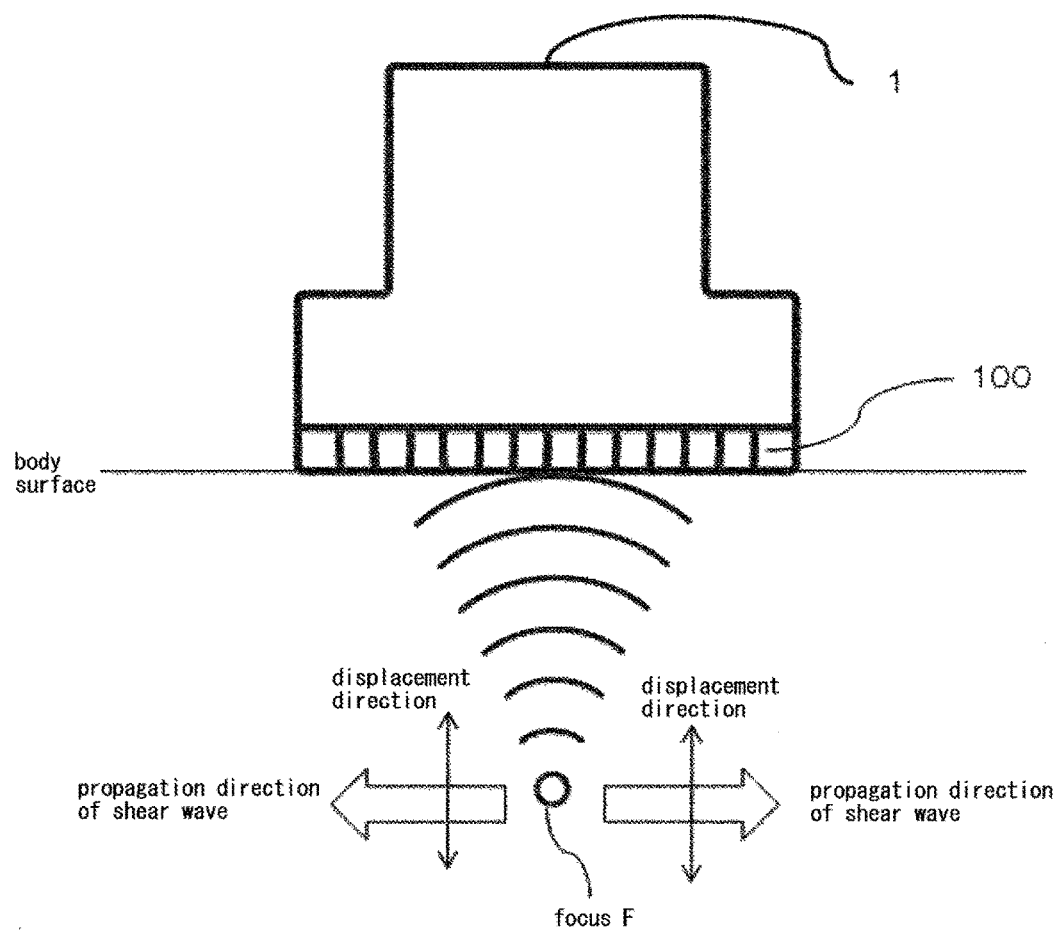
FIG. 2 illustrates a state where a focused beam of ultrasonic waves is converged on a focus F and a shear wave is generated by an ultrasonic probe in the first illustrative embodiment.

As shown in FIG. 2, the ultrasonic diagnostic apparatus of this illustrative embodiment is an apparatus configured to use a method of applying a radiation pressure to the inside of the subject by using a focused beam of ultrasonic waves (the ultrasonic beam for displacement generation=the second ultrasonic beam) transmitted from each element 100 of the ultrasonic probe 1. An example is described below in which the linear array-type ultrasonic probe 1 is contacted to a body surface of a living body, which is the subject, and the second ultrasonic beam (the ultrasonic beam for displacement generation) irradiated from the ultrasonic probe 1 is focused on a desired cross-sectional plane in the living body on the basis of the output of the displacement generation transmission wave beam generation unit 13 of the displacement generation unit 10. Here, it is assumed that a propagation direction of the ultrasonic beam for displacement generation in the desired cross-sectional plane is perpendicular to the body surface. In FIG. 2, an outline arrow indicates a propagation direction of the shear wave and a solid arrow indicates a direction of the displacement.

Figure 3:
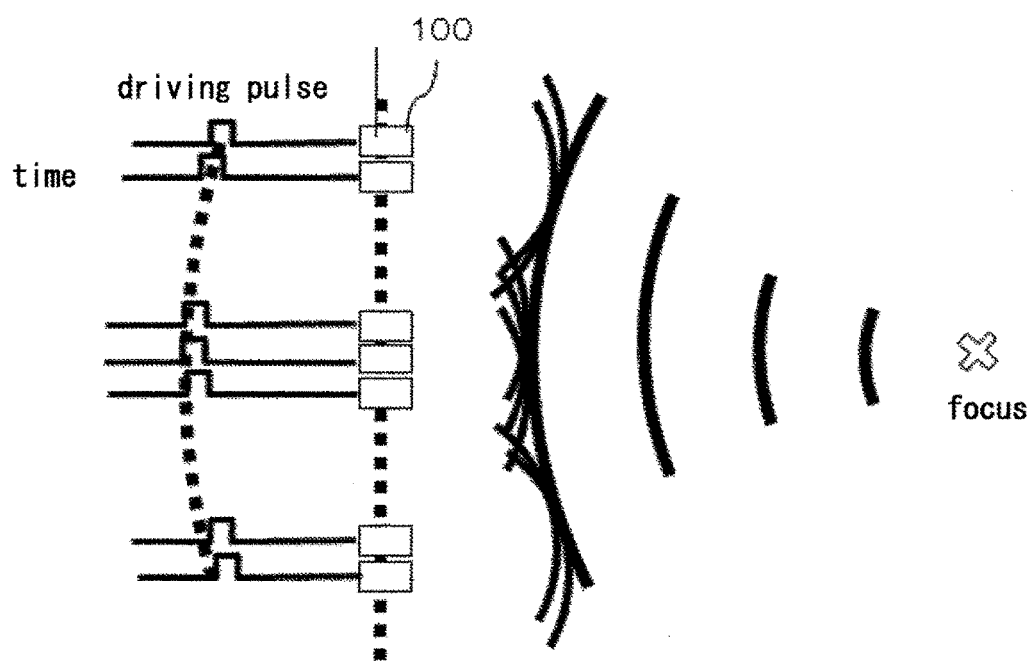
FIG. 3 illustrates a beam forming of an ultrasonic wave in the first illustrative embodiment.
Figure 3:
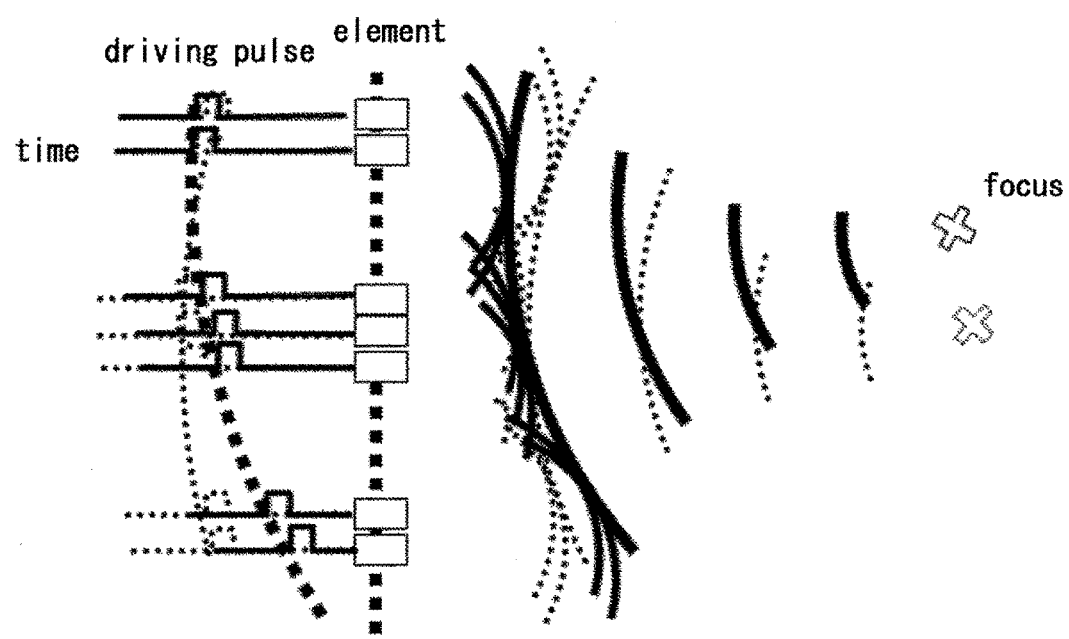

As shown in the upper part of FIG. 3, a beamforming of the ultrasonic beam for displacement generation is implemented by calculating a distance between a focus to which the ultrasonic beam is converged and each element 100 of the ultrasonic probe 1 and applying time, which is calculated by dividing the distance difference between the elements 100 by a sound velocity of a target, to the transmission wave signal for each element 100, as the delay time. When the focused beam is irradiated to the focus, a radiation pressure is generated in correspondence to absorption or scattering of the ultrasonic wave associated with the propagation. Typically, the radiation pressure is the maximum at the focus and a displacement is generated in a living tissue in the focus area. As the radiation pressure is generated, a shear wave beginning at a focused point is generated in a direction parallel with the surface of the subject, as shown in FIG. 2. Also, when the irradiation of the focused beam stops, an amount of the displacement is alleviated. In the meantime, the lower part of FIG. 3 shows a case where the focus position is changed by controlling delay time of driving pulses for the elements 100 of the ultrasonic probe 1. In the meantime, like the ultrasonic beam for displacement generation, a focus position of the ultrasonic beam for displacement detection can be also changed by controlling the delay time of the transmission wave time to be supplied to each element 100. Thereby, it is possible to change the detection position to which the ultrasonic beam for displacement detection is irradiated.

Figure 4:
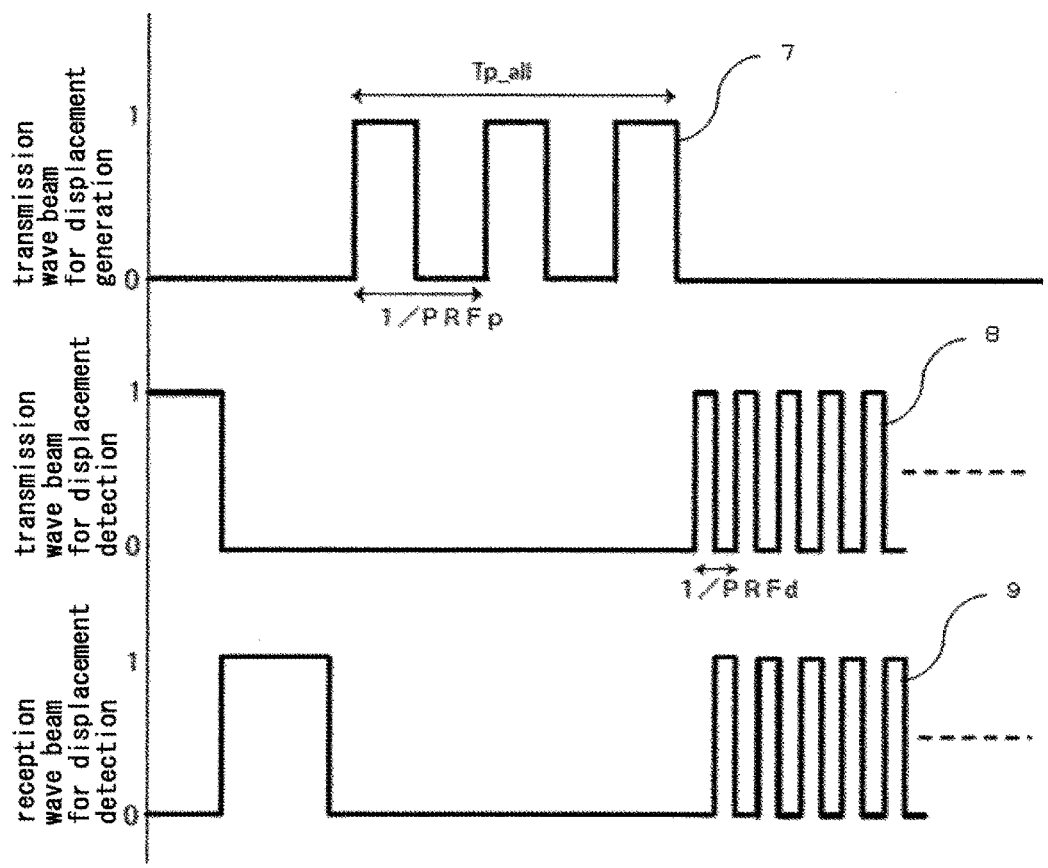
FIG. 4 illustrates a sequence of transmitting and receiving the ultrasonic beam in the first illustrative embodiment.

Subsequently, the method of transmitting and receiving the ultrasonic beam of the ultrasonic diagnostic apparatus of this illustrative embodiment is described with reference to FIG. 4. FIG. 4 pictorially shows irradiation and reception sequences of a transmission wave beam 7 for displacement generation, which is the second ultrasonic beam, a transmission wave beam 8 for displacement detection, which is the first ultrasonic beam, and a reception wave beam 9 for displacement detection of the ultrasonic diagnostic apparatus of this illustrative embodiment. In FIG. 4, 1 in a vertical direction is referred to as ON and 0 is referred to as OFF. The transmission wave beam 7 for displacement generation and the transmission wave beam 8 for displacement detection are irradiated to the focus F and the detection position, respectively, when they are ON. In the meantime, the ON state of the reception wave beam 9 for displacement detection means that the connection of the displacement detection transmission wave beam generation unit 22 and the ultrasonic probe 1 is disconnected and the displacement detection reception wave beam calculation unit 23 is connected to the ultrasonic probe 1 by the transmission and reception changeover switch 2, so that a reception wave signal, which is the echo signal (the reflection signal), is acquired and a phasing addition calculation is performed for beamforming. The switching of the ON and OFF states is performed by controlling the transmission and reception changeover switch 2 with a voltage amplitude value, for example. As shown in FIG. 4, the ON state is first made in order of the transmission wave beam 8 for displacement detection and the reception wave beam 9 for displacement detection and a reference signal, which is used for the calculation of detecting the displacement of the subject tissue caused due to the shear wave and the shear wave velocity, is obtained.

After the reference signal is obtained, the transmission wave beam 7 for displacement generation, which is the second ultrasonic beam, is irradiated to the focus F of FIG. 2, so that a shear wave is generated in the subject tissue. At this time, the irradiation (ON) and non-irradiation (OFF) of the transmission wave beam 7 for displacement generation are repeated with a predetermined frequency $PRF_p$. A value of the frequency $PRF_p$ is set in the beam frequency setting unit 14 of the displacement generation unit 10. Thereby, the measurement can be performed while controlling the ON and OFF frequency $PRF_p$ of the transmission wave beam 7 for displacement generation. A transmission frequency (a frequency of the transmission wave beam, not the repetition frequency $PRF_p$) of the transmission wave beam 7 for displacement generation is set in the vicinity of a central frequency at which the high-sensitive transmission and reception are realized by the ultrasonic probe 1.

In FIG. 4, the number of irradiation (ON) times of the transmission wave beam 7 for displacement generation is three times, for example. However, the number of irradiation times is not limited to three times. As the number of irradiation times is increased, the displacement of the subject tissue is increased. After the transmission wave beam 7 for displacement generation is irradiated, the transmission wave beam 8 for displacement detection and the reception wave beam 9 for displacement detection become ON in order so as to detect the displacement of the subject tissue caused due to the shear wave at the detection position. A signal obtained by the transmission and reception beam for displacement detection is subject to the signal processing such as the bandpass filter and the calculation processing in the wave detection unit 25 of the detection unit 20, and a signal equivalent to the frequency $PRF_p$ is extracted and output as a signal relating to the shear wave.

The calculation of the displacement detection at the detection position is performed using the obtained reference signal and a signal obtained by the transmission and reception wave beams for displacement detection in the waveform analysis unit 26. For the calculation of the displacement detection that is performed in the waveform analysis unit 26, a correlation calculation, a phase detection and the like, which are the well known technologies, are used. The transmission and reception wave beams for displacement detection are repeatedly made to be ON with a repetition frequency $PRF_d$, so that a temporal waveform of the displacement caused due to the shear wave is detected. The frequency $PRF_d$ is set to a sampling interval, for example, ($\frac{1}{10}$)×T that can be sufficiently measured for a period T of the shear wave. The frequency $PRF_d$ is set in the displacement detection transmission wave waveform generation unit 21 of the detection unit 20.

Figure 5A:
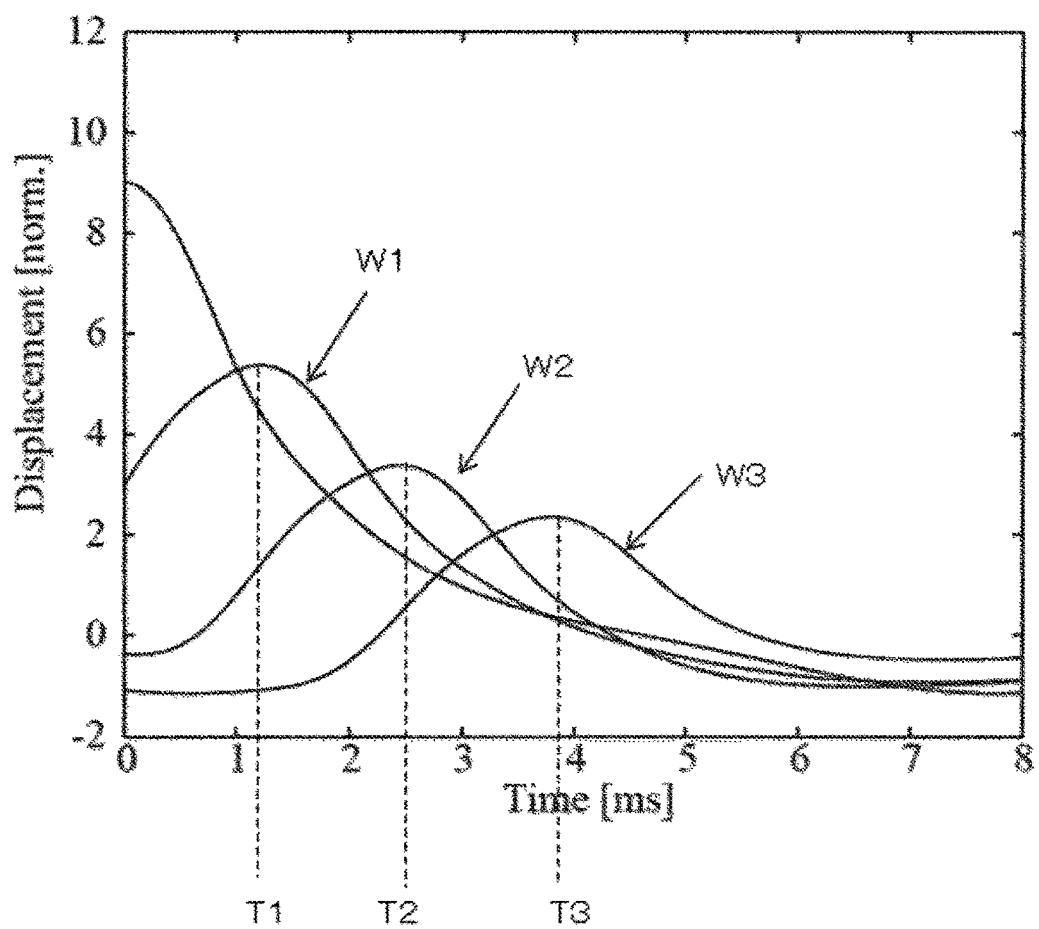
FIG. 5A is a graph showing waveforms of time-variation of displacement resulting from propagation of a shear wave at each detection position in the first illustrative embodiment.

In this illustrative embodiment, the detection position of the displacement is a plurality of positions x1, x2, x3, which are located along the propagation direction of the shear wave parallel with the subject surface and are spaced at an equal interval. Here, the position of the focus F of FIG. 2 is set to be x=0, and x1<x2<x3. FIG. 5A shows examples of temporal waveforms W1, W2, W3 of the shear wave displacement (=an amplitude value of the displacement of the subject tissue caused due to the propagation of the shear wave) at the detection positions x1, x2, x3 of the displacement. In FIG. 5A, the measurement values are shown when the shear wave velocity is 3 m/s and x1=1.2 mm, x2=2.5 mm and x3=3.8 mm. From FIG. 5A, it can be seen that as the detection position becomes more distant from the focus, the time at which the shear wave peaks is delayed. As shown in FIG. 5B, the hardness information calculation unit 28 of the control unit 3 is configured to calculate a gradient of an approximation straight line 50, which is obtained by a linear approximation of the peak time and the detection position of the shear wave, from a graph of the peak time and the detection position, thereby calculating a shear wave velocity, which is a parameter indicating the hardness on the basis of output of the waveform analysis unit 26.

In the meantime, as described later, the shear wave velocity that is calculated using a peak value or zero cross value is a group velocity. That is, in this illustrative embodiment, the control unit 3 is configured to calculate a group velocity of the shear wave on the basis of the peak value or zero cross value of the shear wave, and to calculate the hardness information of the subject on the basis of the group velocity. As described later, a phase velocity and a viscosity of the shear wave are calculated on the basis of a spectrum value of the shear wave and the hardness information may be calculated on the basis of the phase velocity and the viscosity. An operator can set (select) the group velocity of the shear wave, and the phase velocity and the viscosity of the shear wave, as the hardness information to be obtained, by the input unit 6.

Figure 6:
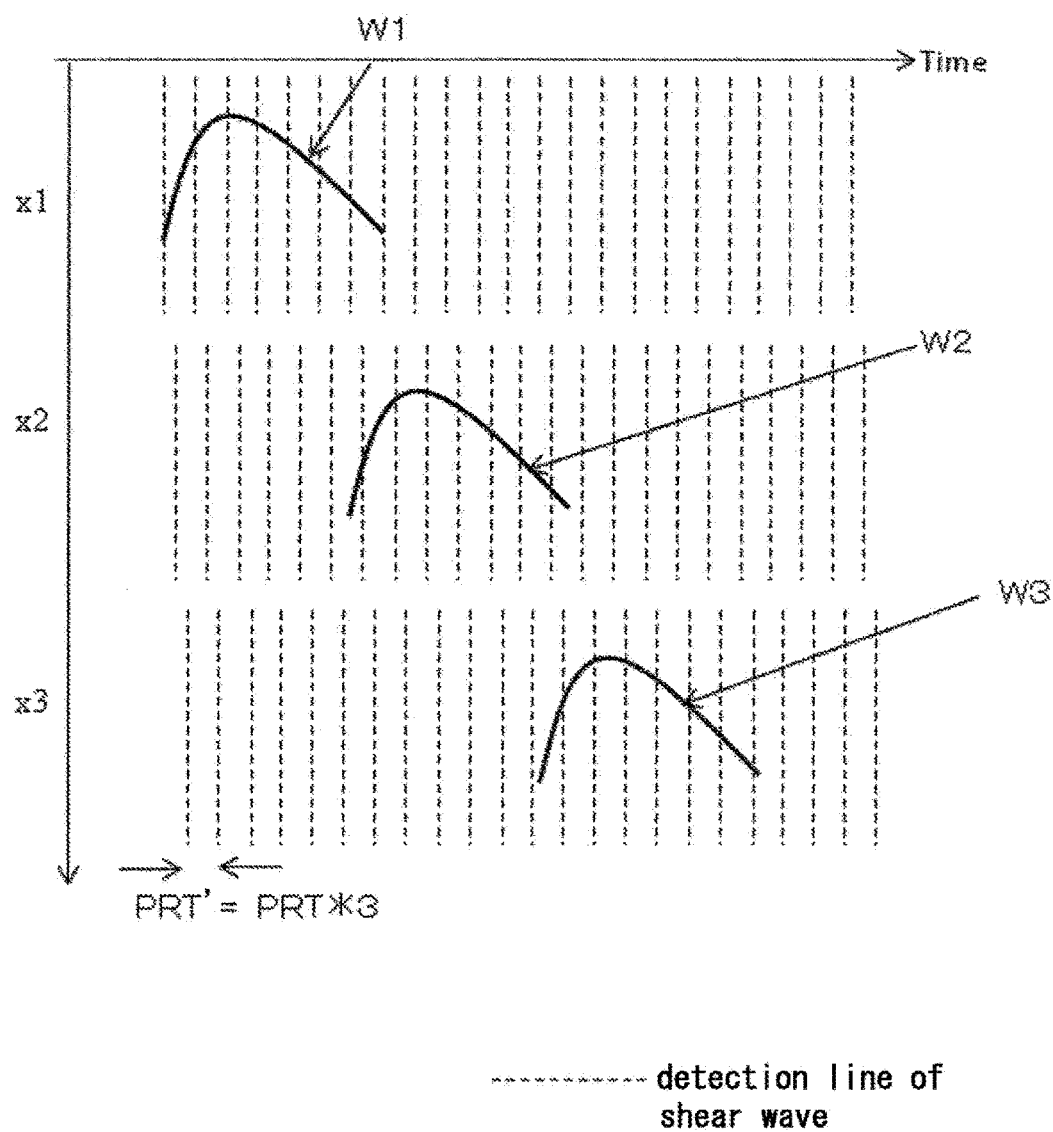
FIG. 6 illustrates a sequence of detection timings of shear waves at detection positions X1, X2, X3 in the related art.

A conventional technology (parallel tracking technology) of detecting the displacement caused due to the shear wave at the plurality of detection positions x1, x2, x3 is described with reference to FIG. 6. In this technology, an operation of irradiating the ultrasonic beam for displacement detection in parallel in a time-division manner to the plurality of detection positions x1, x2, x3 is repeated for an entire measurement time period, so that the displacement at the plurality of detection positions is detected at the same time for the entire measurement time period. That is, the operation of irradiating the ultrasonic beam for displacement detection in order of the respective detection positions x1, x2, x3, x1, x2, x3 . . . is repeated for the measurement time period. A vertical axis in FIG. 6 indicates a detection position and displacement at the detection position, and a horizontal axis indicates the measurement time. A dotted line indicates a detection line (irradiation timing of the ultrasonic for displacement detection) of the shear wave in a time direction. Also, in FIG. 6, curves indicating the shear waves W1, W2, W3 indicate waveforms (displacement) of the shear waves arriving at the detection positions x1, x2, x3. Therefore, it can be seen that a displacement amount of the shear wave is detected at a position at which the detection line and the curves of the shear waves W1, W2, W3 intersect as shown in FIG. 6, for the entire measurement time period. As shown in FIG. 6, the displacement of the shear wave is detected at the respective detection positions x1, x2, x3 at an equal time interval PRT'.

A time resolution of the shear wave displacement detection is described. The time resolution of the shear wave displacement detection is limited by a pulse repetition time (PRT) of the ultrasonic beam for displacement detection. That is, since it is not possible to detect the displacement of the shear wave with a period less than the PRT of the ultrasonic beam for displacement detection, the minimum time resolution is the PRT. As shown in FIG. 4, the PRT of the ultrasonic beam for displacement detection is 1/PRFd, and when the detection position of the shear wave is only one, it is possible to irradiate the ultrasonic beam for displacement detection to the corresponding detection position with the PRT, so that the minimum time resolution is the same as the PRT. However, as shown in FIG. 6, when the ultrasonic beam for displacement detection is irradiated in parallel to the three detection positions x1, x2, x3, since the detection positions are three places, a period during which the ultrasonic beam for displacement detection can be irradiated to one detection position is three times greater than the PRT. Therefore, the minimum time resolution PRT' at each detection position is PRT*3.

Subsequently, a detection sequence of the shear wave at the plurality of detection positions in this illustrative embodiment is described with reference to FIG. 7. In the ultrasonic diagnostic apparatus of this illustrative embodiment, a measurement time period is allotted to each detection position by using a fact that there is a time difference in arrival time of the shear wave at the plurality of detection positions, and the shear wave is detected at only one detection position for one measurement time period. The switching of the detection position at which the shear wave is measured is controlled on the basis of the output of the waveform analysis unit 26. Specifically, first, the ultrasonic beam for displacement detection, which is the first ultrasonic beam, is transmitted to only the detection position x1 with the minimum period (PRT) during which the ultrasonic beam can be irradiated, so that the displacement of the shear wave W1 is detected at the detection position x1 (the measurement time period of the detection position x1). At this time, the detection is not performed at the other detection positions x2, x3. When a peak value of a temporal waveform of the displacement of the shear wave W1 is detected at the detection position x1, the detection at the detection position x1 is over, and at the same time, the ultrasonic beam for displacement detection, which is the first ultrasonic beam, is transmitted to the detection position x2 with the minimum period (PRT) during which the ultrasonic beam can be irradiated, so that the detection of the shear wave W2 at the detection position x2 is performed (the measurement time period of the detection position x2). Likewise, when a peak value of the displacement of the shear wave W2 is detected at the detection position x2, the detection of the shear wave at the detection position x2 is over, and at the same time, the ultrasonic beam for displacement detection, which is the first ultrasonic beam, is transmitted to the detection position x3 with the minimum period (PRT) during which the ultrasonic beam can be irradiated, so that the detection of the shear wave W3 at the detection position x3 is performed (the measurement time period of the detection position x3). When a peak value of the shear wave W3 is detected at the detection position x3, the detection of the shear wave W3 is over.

In this illustrative embodiment, the peak value of the displacement of the shear wave is detected by the waveform analysis unit 26 of the control unit 3, for example, the CPU by using the well-known technology such as HPF (High Pass Filter). In the above descriptions, the number of the detection positions is three. However, the number of the detection positions is not limited thereto.

In the detection sequence of the shear wave at the plurality of detection positions according to this illustrative embodiment, the fact that there is a time difference in arrival time of the shear wave at the plurality of detection positions is used and thus the ultrasonic beam for displacement detection is continuously irradiated to only one detection position until the peak of the displacement of the shear wave at the one detection position is detected. Therefore, the time resolution PRT' of the displacement detection of the shear wave is the same as the PRT. The irradiation position of the ultrasonic beam for displacement detection is moved to a next detection position at timing at which the peak is detected, so that it is possible to detect the peak of the displacement of the shear wave at each detection position. Therefore, it is possible to detect the shear wave at the plurality of detection positions, to obtain the shear wave velocity from the shear wave displacement detected from the plurality of detection positions and to calculate the hardness information without lowering the time resolution and the spatial resolution of the shear wave detection.

Subsequently, a processing flow of the shear wave velocity calculation is described, which is performed in the waveform analysis unit 26, the hardness information calculation unit 28 and the central control unit 29 of the control unit 3 of the ultrasonic diagnostic apparatus according to the first illustrative embodiment, with reference to FIG. 8. First, in the flowchart of FIG. 8, the measurement starts in step S00. Here, an operator sets a hardness measuring range (ROI: Region of Interest) while seeing a cross-sectional image displayed on the display unit 5, for example, a B mode image or strain image, and pushes a start switch in a GUI (Graphic User Interface) on a display screen of the display unit 5 or a start switch of the input unit 6. The range may be set through the display screen of the display unit 5 or the input unit 6 such as a track ball, a mouse, a keyboard, a touch panel and the like. Alternatively, the control unit 3 may read out a position corresponding to a measurement part such as the liver, the mammary gland and the like from the memory (not shown), which is a storage device, thereby setting the range. The start switch is arranged on a panel, which is the input unit 6 of the ultrasonic diagnostic apparatus. The detection positions x1, x2, x3 . . . xn are set within the ROI set by the operator. The specific position of the detection position such as an interval of the detection positions can be automatically set by the control unit 3 or can be set through the input unit 6 by the operator.

Figure 7:
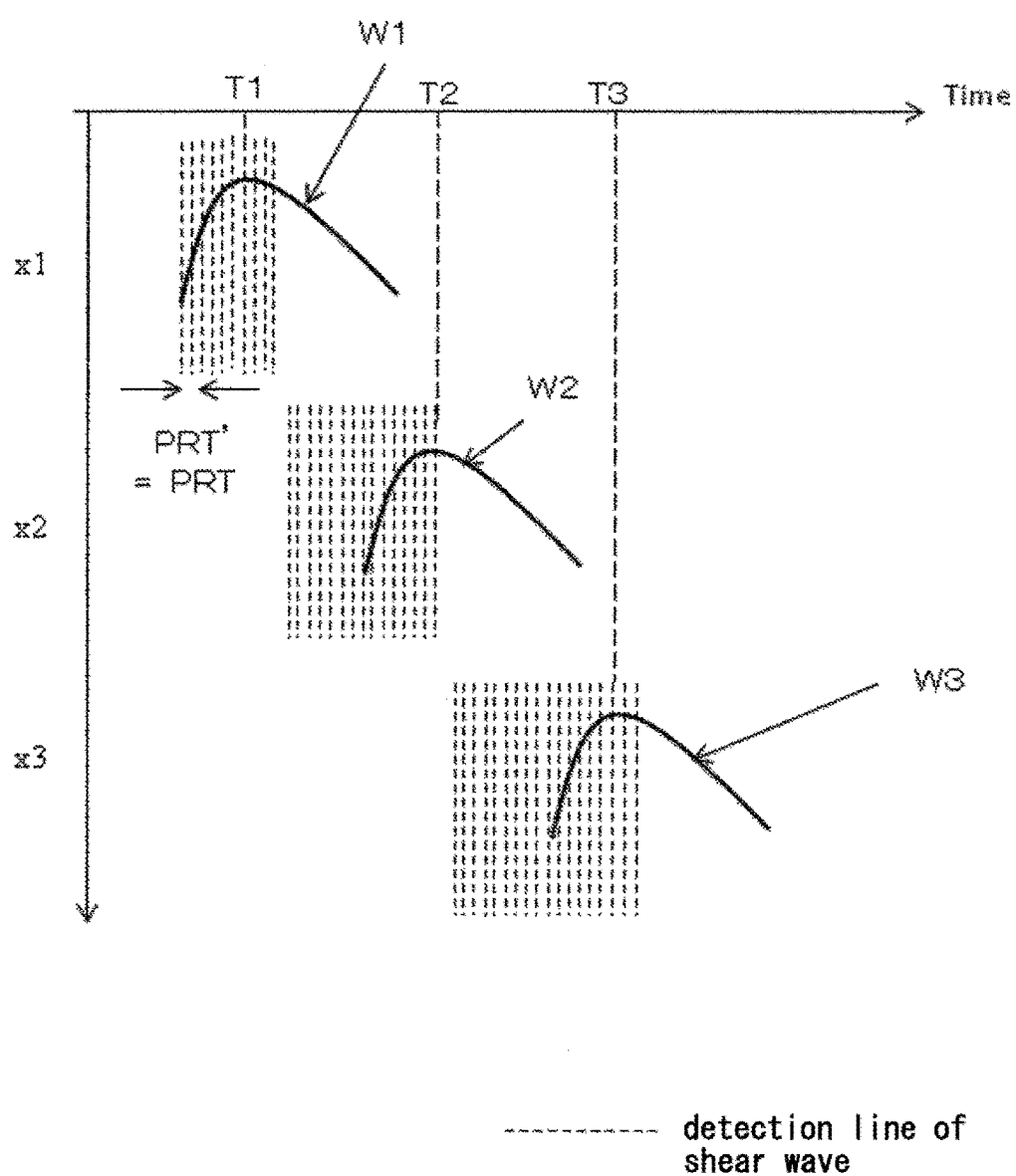
FIG. 7 illustrates a sequence of detection timings of the shear waves at the detection positions X1, X2, X3 in the first illustrative embodiment.

Then, in step S10, the detection of the shear wave W1 at the detection position x1 shown in FIG. 7 starts. The displacement detection transmission wave beam generation unit 22 irradiates the ultrasonic beam for displacement detection, which is the first ultrasonic beam, to the detection position x1 at a time interval of the PRT, the displacement detection reception wave beam calculation unit 23 receives a reflected wave from the subject, and the waveform analysis unit 26 calculates the displacement and detects a peak via the wave detection unit 25.

Figure 8:
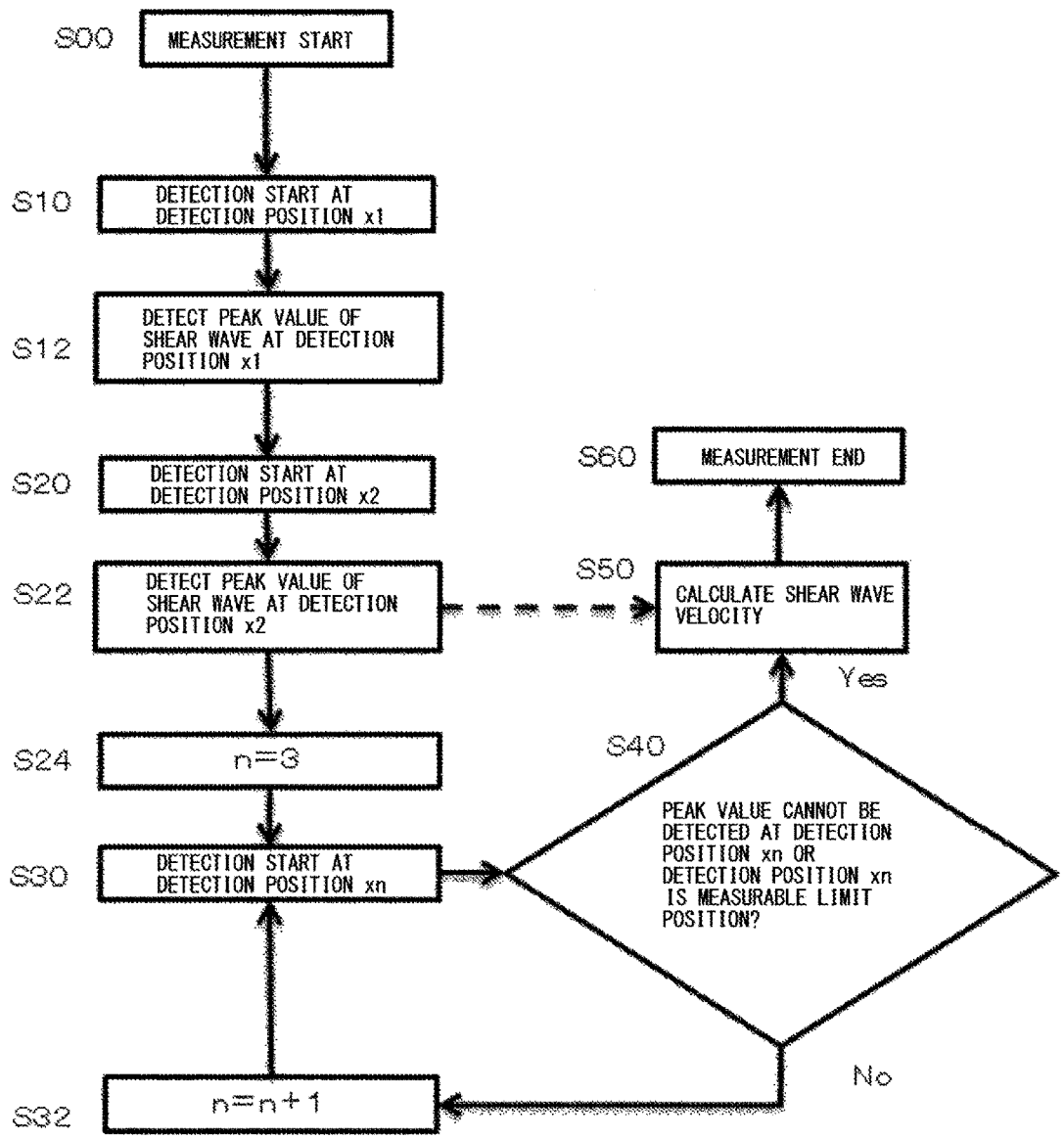
FIG. 8 is a flowchart showing a shear wave detection operation in first and second illustrative embodiments.

In step S12 of FIG. 8, the beam for displacement detection is continuously transmitted and received at the detection position x1 until a peak value of the shear wave W1 is detected at the detection position x1. In the configuration of this illustrative embodiment, when a peak value of the shear wave is detected at the waveform analysis unit 26 of the control unit 3, a signal for setting a next displacement detection position to the detection position x2 is output from the waveform analysis unit 26 to the displacement detection transmission wave beam generation unit 22 directly or via the central control unit 29.

That is, according to the apparatus of this illustrative embodiment, based on the signal from the waveform analysis unit of the control unit 3, the displacement detection transmission wave beam generation unit 22 of the detection unit 20 can switch the detection time at which the ultrasonic beam for displacement detection is transmitted to each of the detection positions x1, x2, x3 . . . . In other words, it is possible to dynamically switch the detection position at which the displacement is detected, depending on the output of the detection unit 20. Also, the first detection position x1 and the time T1 at which a peak value is made, which are shown in FIG. 7, are recorded in the memory (not shown) by the central control unit 29. The detection unit 20 can set the time at which the ultrasonic beam for displacement detection is transmitted to the second detection position x2, i.e., the time at which the detection position is dynamically switched to the second detection position x2, depending on an analysis result of the shear wave at the first detection position.

Then, in step S20, like step S10, the detection of the shear wave at the detection position x2 starts. Also, in step S22, the same processing as step S12 is executed for the shear wave W2 detected at the detection position x2. When a peak value is detected at the detection position x2, the detection position x2 and the time T2 at which the peak value is made are recorded in the memory (not shown) by the control unit 3. For the calculation of the shear wave velocity in the hardness information calculation unit 28, at least two detection positions and peak time are required, as can be clearly seen from FIG. 5B. When the measurement is over at two places, the shear wave velocity is calculated in step S50. The shear wave velocity is calculated in the hardness information calculation unit 28 by using the peak time and detection position obtained from the waveform analysis unit 26. A value calculated at the hardness information calculation unit 28 is the hardness information such as a shear viscosity, a Young's modulus, a shear wave elastic coefficient and the like, in addition to the shear wave velocity. When the calculation of the hardness information such as the shear wave velocity is over in the hardness information calculation unit 28, the measurement is over in step S60 and the value or image relating to the hardness information is displayed on the display unit 5.

In order to calculate the shear wave velocity, which is the hardness information, with high precision, the measurement is performed with the number of the detection positions being increased. In this case, after the peak value at the detection position x2 is detected, a next detection position is designated in step S24. Here, this means that a detection position xn (n=3) corresponding to the detection number n(=3) is output to the displacement detection transmission wave beam generation unit 22 by the waveform analysis unit 26. In step S30, the detection position by the ultrasonic beam for displacement detection, which is transmitted from the displacement detection transmission wave beam generation unit 22, is dynamically switched, so that the peak detection of the shear wave W3 at the detection position x3 starts. In step S40, when a peak cannot be detected at the detection position x3 or the detection position x3 reaches a limit of a measurable position, the shear wave velocity is estimated in step S50 and the measurement is over in step S60.

In the meantime, the description that a peak cannot be detected means that the phase or displacement amount obtained by the correlation calculation in the waveform analysis unit 26 is below a noise caused due to an influence of the pulse wave and the like. Also, the limit of a measurable position is a position of the beam for displacement detection generated in the ultrasonic probe 1 or a pre-designated position. The designation of the position is made by an input of the operator through the input unit 6 or by the readout of the central control unit 29 of the control unit 3 from the memory (not shown). In step S40, when it is not determined that a peak cannot be detected at the detection position x3 and that the detection position x3 reaches a limit of a measurable position, a next detection position xn (n=n+1) is designated in the waveform analysis unit 26 by using the approximation straight line 50 shown in FIG. 5B in step S32, and the detection of the shear wave at the detection position xn starts in step S30.

Figure 9:
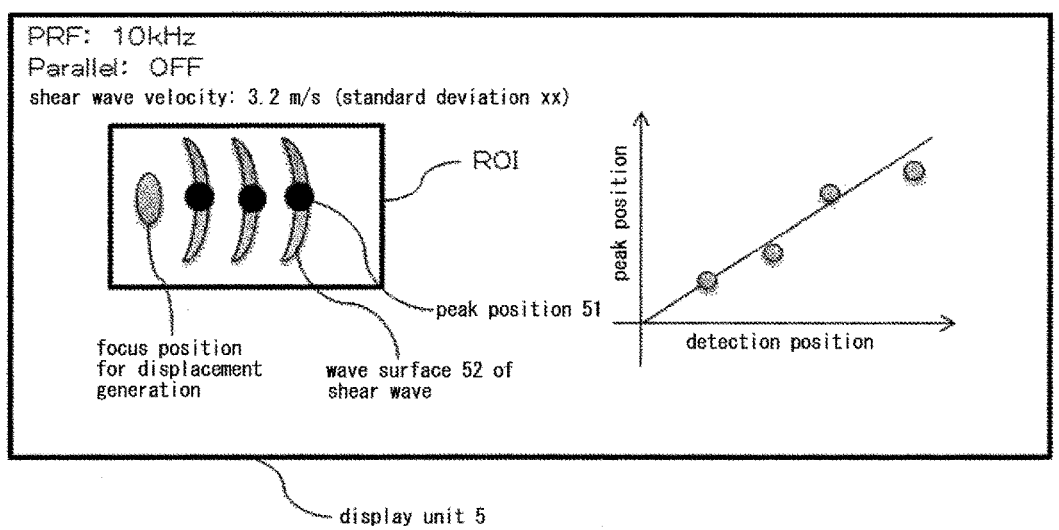
FIG. 9 illustrates an example of a display screen of a hardness measurement result on a display unit 5 in the first illustrative embodiment.

FIG. 9 illustrates an example of a display screen of a hardness measurement result measured in the hardness information calculation unit 28 of the apparatus of this illustrative embodiment and output to the display unit 5. The display unit 5 displays the hardness information. Also, the display unit 5 can display a degree of reliability of the hardness information and can display, as the degree of reliability, a standard deviation, a correlation function of waveforms of two or more shear waves, and the like. Further, it is possible to display the pulse repetition time (PRT) or pulse repetition frequency of the first ultrasonic beam.

FIG. 9 illustrates a peak position 51 and a wave surface 52 of the shear wave when the shear wave is detected with the linear array-type probe. On the display unit 5, a value of the shear wave velocity estimated within the ROI, a value of the standard deviation indicating a degree of reliability of the value, and the like are displayed together. Also, a graph showing a relation between the peak position and the detection position is displayed at the right of the display screen of FIG. 9. From FIG. 9, the operator can check with eyes whether the measurement is correctly performed. Also, an effective PRT, which is the time resolution of the shear wave measurement, or a PRF, which is an inverse of the PRT, may be displayed on the display screen of the display unit 5. A color mapping may be displayed by displaying a difference in the shear wave velocity with a color value on the basis of a plurality of measurement results. In this case, a color scaling function may be added to the configuration of the ultrasonic diagnostic apparatus shown in FIG. 1.

As shown in FIG. 9, the shear wave velocity, which is the hardness information of the subject calculated and output by the control unit 3, the standard deviation, which indicates the degree of reliability of the shear wave velocity, the PRT, the PRF, the information (ON, OFF) indicating whether the parallel tracking method is applied or not, the wave surface 52 of the shear wave, the peak position 51 of the shear wave, and the like are displayed on the display screen of the display unit 5 of this illustrative embodiment, which can improve the convenience of the user.

Subsequently, a method of setting the interval of the detection positions x1, x2, x3 . . . xn in the ultrasonic diagnostic apparatus of this illustrative embodiment is described. In the apparatus of this illustrative embodiment, the control unit 3 can set the interval of the detection positions. Also, the operator can set the interval of the detection positions through the input unit 6. For example, the interval of the detection positions is ½λ to λ when a wavelength of the shear wave is denoted with λ. The wavelength is determined from the shear wave velocity assumed at a measurement target part and the irradiation time information of the focused beam for displacement generation. For example, when measuring the liver, the shear wave velocity in the liver is about 1 to 5 m/s. When the irradiation time of the focused beam is set to 0.5 ms, a period of the focused beam is 2×0.5 (=1 ms). At this time, the wavelength can be calculated by multiplying the shear wave velocity and the period and is about 1 to 5 mm. Therefore, the control unit 3 sets an interval of the deposition positions of the shear wave within a range of 0.5 mm to 5 mm.

Also, as described above, the interval of the detection positions may be input by the operator through the display unit 5 capable of functioning as an input unit or the input unit 6. That is, the display unit 5 and the input unit 6 shown in FIG. 1 can set the interval of the detection positions. In this case, the operator can manually flexibly change the interval of the detection positions, based on the measurement result. Alternatively, the interval of the detection positions can be automatically set. In this case, the setting of the interval of the detection positions is performed by a processing unit, which is the waveform analysis unit 26 of the control unit 3. The interval of the detection positions may be changed to measure the hardness, and an average value, a variance value and the like of the hardness for the changed interval of the detection positions may be displayed on the display unit 5.

Figure 10:
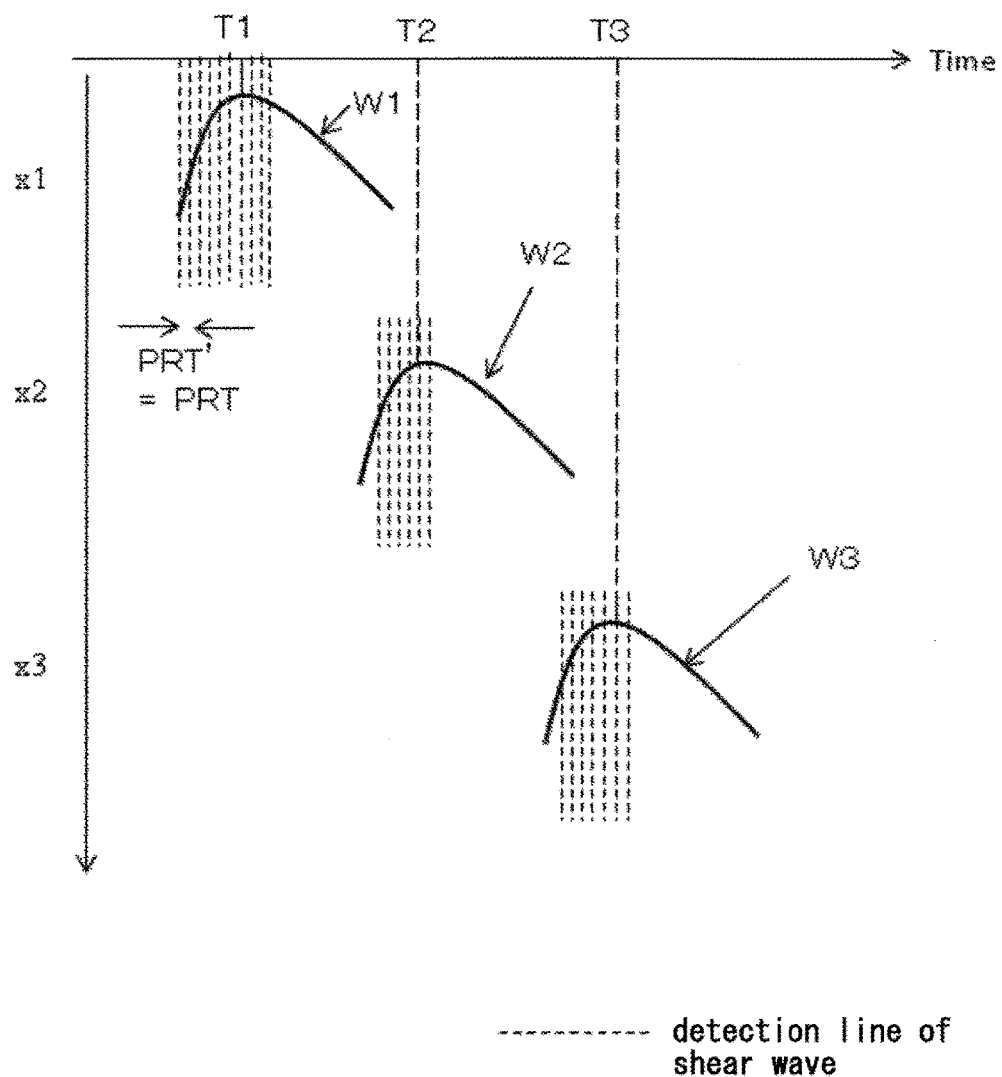
FIG. 10 illustrates a sequence of detection timings of the shear waves at the detection positions X1, X2, X3 in an application embodiment of the first illustrative embodiment.

Subsequently, a modified embodiment of this illustrative embodiment is described with reference to FIG. 10. In this modified embodiment, time at which the first ultrasonic beam is transmitted to a second detection position is set based on the detection result of the shear wave, which is the output of the detection unit 20 at a first detection position. In FIG. 7, the peak is detected at the detection position x1, and at the same time, the detection starts at the detection position x2. In FIG. 10, peak time T2 at the detection position x2 is estimated on the basis of the detection position x1, the peak time T1 and irradiation time information of the focused beam for displacement generation. Here, the irradiation time information is irradiation starting time, irradiation time or irradiation ending time. Then, the displacement detection starts from t(=T2−N×PRT) (N is any positive integer) at the detection position x2. In this modified embodiment, since it is possible to reduce the number of the detection lines of the shear wave, it is possible to reduce the calculation processing cost.

Figure 11A:
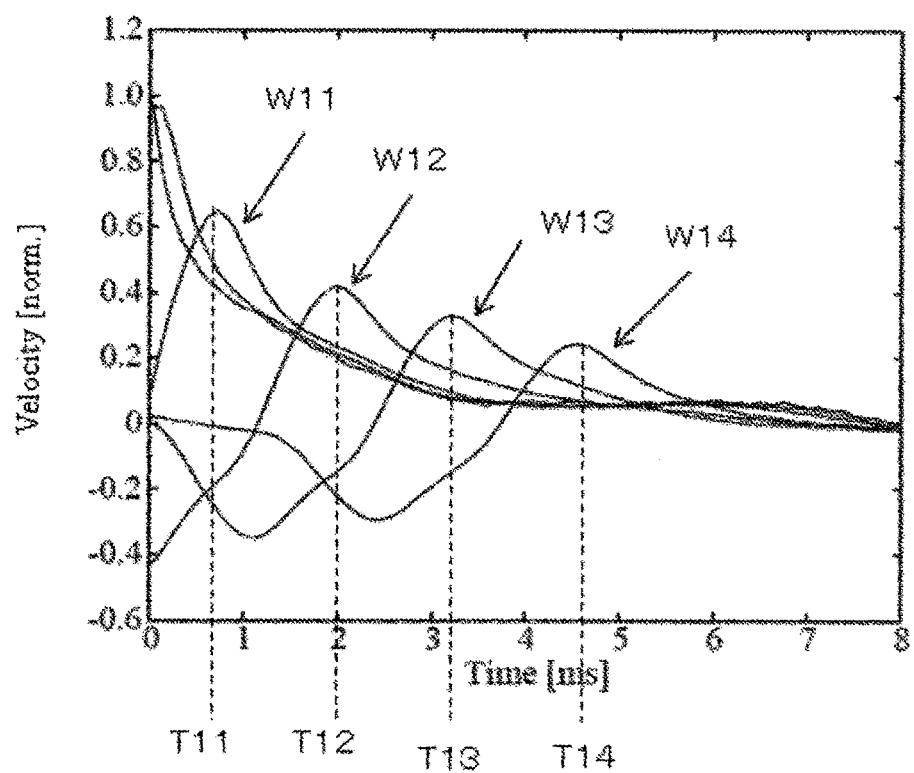
FIG. 11A is a graph showing waveforms of time-variation of a particle velocity of the shear wave at each detection position in the first illustrative embodiment.
Figure 11B:
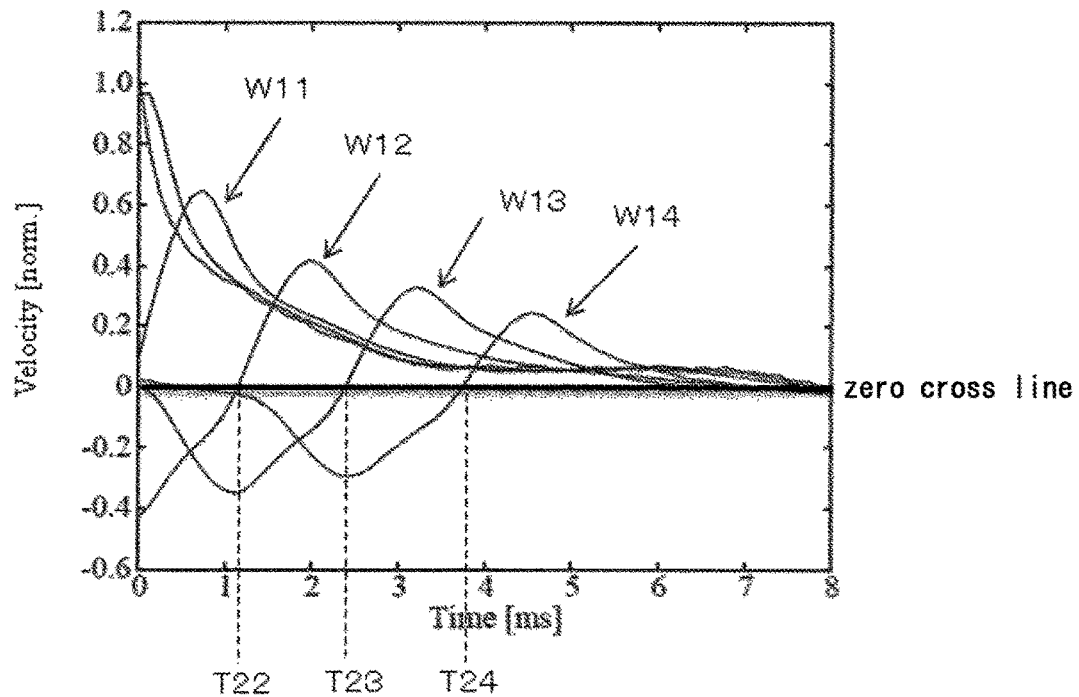
FIG. 11B is a graph showing another example of waveforms of time-variation of the particle velocity of the shear wave at each detection position in the first illustrative embodiment.

In the above-described first illustrative embodiment, the method of detecting the peak value of the waveform of the displacement of the shear wave has been described. However, a particle velocity, a particle acceleration, a phase and a phase velocity, rather than the displacement, may be also used. FIGS. 11A and 11B illustrate the particle velocity (Velocity) of the shear wave shown in FIG. 5A, i.e., the displacement of the shear wave/PRT. At this time, it should be noted that the particle velocity is different from the propagation velocity of the shear wave, which is a value to be measured. In the case of the particle velocity, three parameters of a positive peak, a negative peak and a zero cross value exist per one detection position. Among the parameters, one or more parameters may be used to estimate the group velocity of the shear wave, as the shear wave velocity.

FIG. 11A illustrates time T11, T12, T13, T14 at which positive peaks are made in particle velocity waveforms W11, W12, W13, W14 of the shear waves. Also, FIG. 11B illustrates time T22, T23, T24 at which zero cross values are made. A merit of using the particle velocity is that when the positive peak is detected, the detectable numbers are increased, as compared to the configuration where the peak is detected from the displacement. Also, since the waveform of the shear wave is steeper, it is possible to detect the peak robustly against a variation due to a body motion and the like.

In the meantime, the particle velocity and the particle acceleration may be detected using a filter configured to detect a gradient or outline, for example, gradient filter processing, Laplacian filter processing and the like, which are the well-known technologies as regards the signal processing of the temporal waveform of the shear wave.

In this way, when the shear wave is detected using the particle velocity or particle acceleration, the zero cross value and the like may be used in addition to the peak value, as the value detected in the measurement flow of FIG. 8.

According to the ultrasonic diagnostic apparatus of the first illustrative embodiment, it is possible to measure the shear wave with the high time resolution and spatial resolution. Thereby, it is possible to estimate the shear wave velocity and to evaluate the hardness with high precision. Also, since it is possible to suppress the time, which is required to detect the shear wave at each measurement position, to the minimum, it is possible to reduce the calculation cost. Further, since it is possible to determine the next detection position or time from the waveform of the shear wave observed at any one measurement position, it is possible to maximize the PRT per one place.

Second Illustrative Embodiment

Subsequently, a second illustrative embodiment is described. The second illustrative embodiment is an illustrative embodiment of the ultrasonic diagnostic apparatus capable of evaluating the frequency dependency of the shear wave. In the meantime, the configuration of the ultrasonic diagnostic apparatus of the second illustrative embodiment is the same as the apparatus configuration of the first illustrative embodiment shown in FIG. 1.

In the first illustrative embodiment, the hardness information is measured using only the peak position and peak time of the shear wave. The shear wave velocity obtained in this case is a value relating to the group velocity. On the one hand, there is a viscosity, as the frequency depending parameter of the hardness information. The frequency described here means a frequency of the shear wave. In general, since the living tissue has the viscosity, the shear wave velocity has the frequency dependency. In order to evaluate the frequency dependency of the shear wave velocity, an entire waveform of the shear wave is detected and spectrum-analyzed to calculate spectrum values. In order to perform the spectrum analysis, the FFT analysis, which is the well-known technology, and the like are used. In this illustrative embodiment, the detection unit 20 can calculate a phase velocity and a viscosity of the shear wave on the basis of the spectrum values of the shear wave and estimate the hardness information of the subject on the basis of the phase velocity and the viscosity.

Figure 12A:
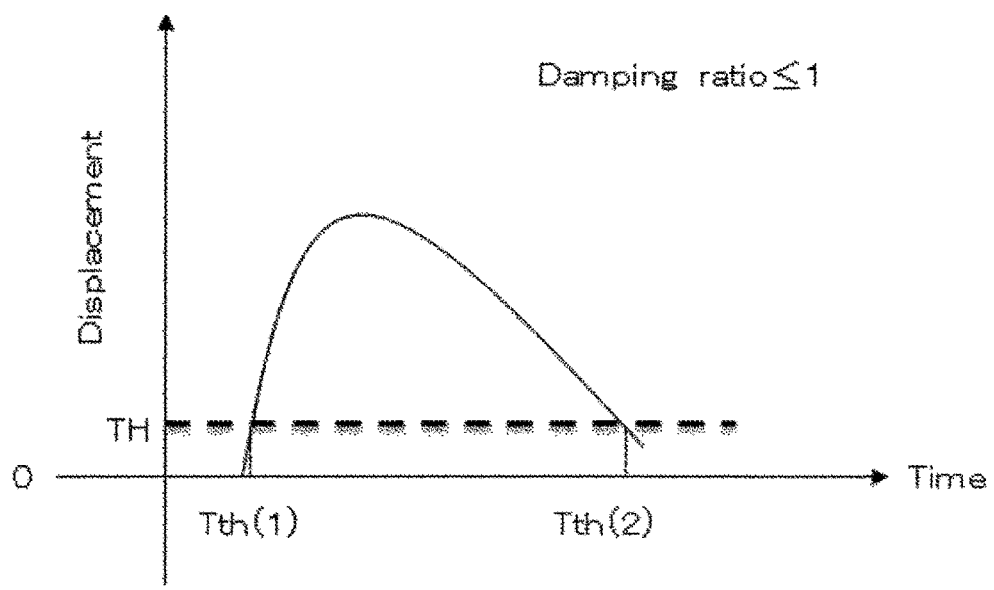
FIG. 12A illustrates a relation between a temporal waveform of the displacement of the shear wave and a threshold TH when a damping ratio is equal to or smaller than 1 in the first illustrative embodiment.
Figure 12B:
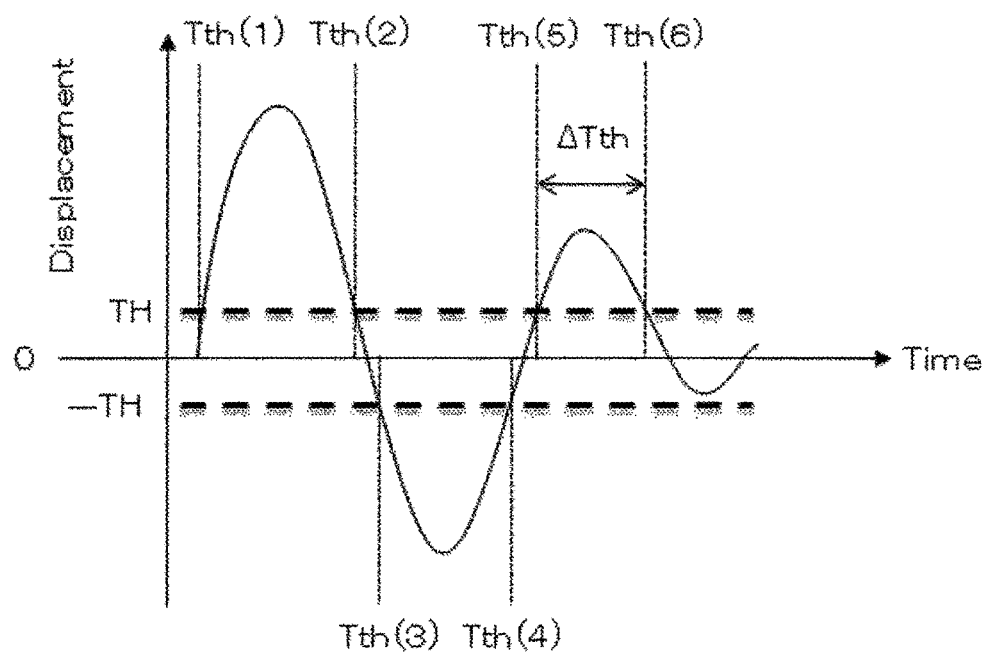
FIG. 12B illustrates a relation between a temporal waveform of the displacement of the shear wave and a threshold TH, −TH when the damping ratio is larger than 1 in the first illustrative embodiment.

Further, a time response of the shear wave is different depending on a damping ratio. FIGS. 12A and 12B illustrate time waveforms of the shear wave resulting from a difference in the damping ratio. FIG. 12A illustrates a time response waveform when the damping ratio is equal to or smaller than 1, and FIG. 12B illustrates a time response waveform when the damping ratio is larger than 1.

Figure 13:
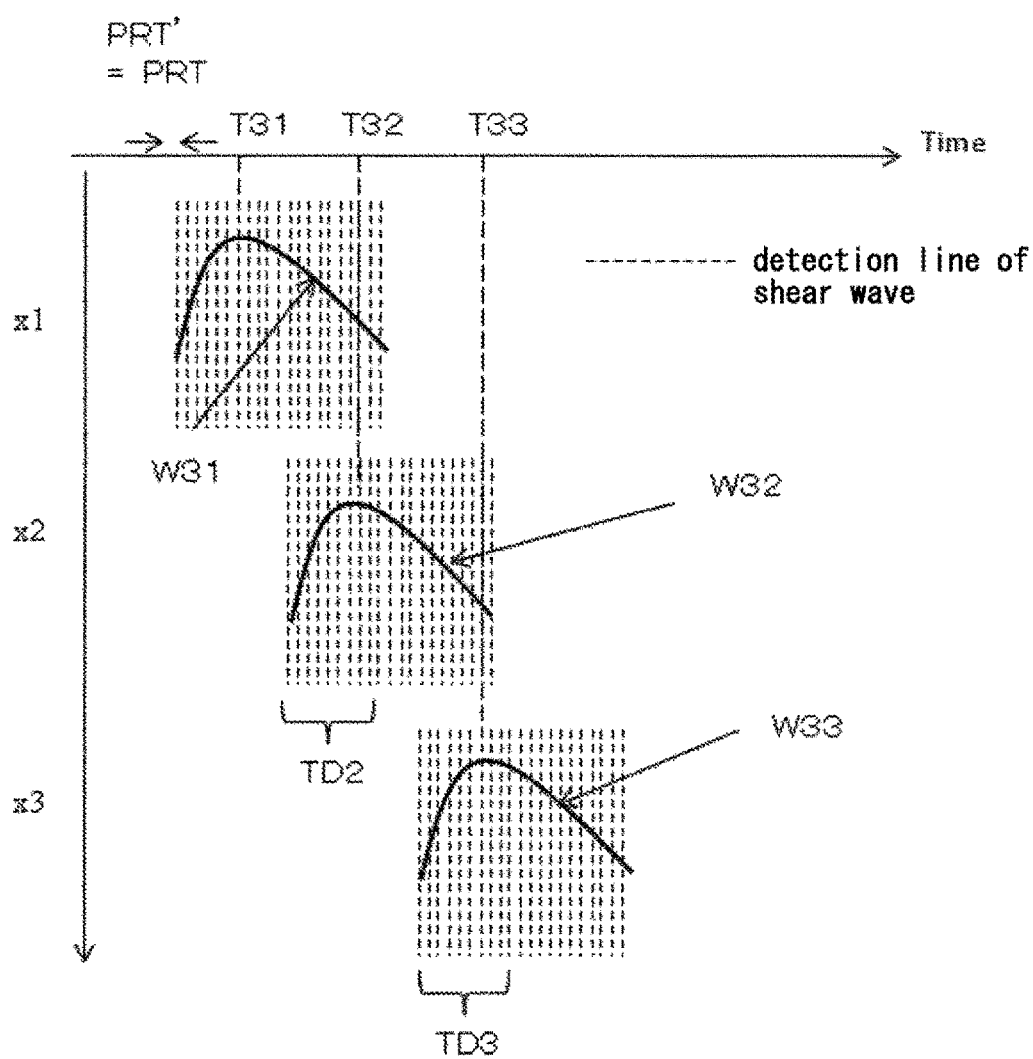
FIG. 13 illustrates a sequence of detection timings of the shear waves at the detection positions X1, X2, X3 in a second illustrative embodiment.

FIG. 13 illustrates a detection sequence of the shear wave according to the second illustrative embodiment. Like the first illustrative embodiment, the detection sequence can be also implemented by the program processing of the CPU configuring the waveform analysis unit 26, the hardness information calculation unit 28 and the central control unit 29. At the respective detection positions x1, x2, x3, the displacement measurement is continuously performed until the measurement of the entire waveform is over, even after time T31, T32, T33 at which the peak values of the shear waves W31, W32, W33 are detected. The measurement position is changed after the measurement of the entire waveform is over. As shown in FIGS. 12A and 12B, the ending time of the entire waveform is set to time at which an absolute value of the displacement becomes smaller than an absolute value |TH| of any threshold±TH. When the displacement is positive, the threshold is positive, and when the displacement is negative, the threshold is negative. As the threshold, a detectable minimum displacement amount, i.e., about 0.05 μm is used, for example.

In the case of the waveform shown in FIG. 12A, the displacement of the shear wave becomes larger than the threshold TH at time Tth(1), increases over time, becomes maximum and then decreases, and becomes smaller than the threshold TH at time Tth(2). At this time, time Tth(2) is set as the measurement ending time.

Also, in the case of the waveform shown in FIG. 12B, the damping ratio is larger than 1, and the displacement repeatedly becomes negative and positive over time. In this case, the time becoming a candidate of the measurement ending is time Tth(2), Tth(4) and Tth(6). When it is desired to measure the group velocity, the earliest time of the time candidates is used as the ending time. In the meantime, when the measurement is performed including the frequency component, since the entire waveform is the measurement target, the latest time Tth(6) is used. At this time, the latest time Tth(6) is determined as time from which an absolute value of the displacement is not larger than the absolute value of the threshold even when the same time as time ΔTth (=Tth(6)−Tth(5)) elapses from the time Tth(6).

On the other hand, even when the positive/negative of the displacement of FIGS. 12A and 12B are reverse, the ending time can be determined in the same manner. When the measurement target is the particle velocity, the particle acceleration, the phase or the phase velocity, the threshold to be set is changed in conformity to the parameter to be measured.

In the meantime, as shown in FIG. 13, in order to measure the entire waveform of the shear wave, there may be time zones (TD2, TD3) during which the measurement is performed at the same time at two detection positions. That is, there is a time zone during which the measurement time periods at the two detection positions overlap. In this case, the parallel tracking method (refer to NPL 1) that is the well known technology is applied only for the time zones (TD2, TD3) during which the measurement is performed at the same time at two detection positions. At this time, PRT' is PRT*2. For the other measurement time zones, the measurement is performed with PRT'=PRT, like the first illustrative embodiment. Meanwhile, according to this illustrative embodiment where the parallel tracking method is applied at two detection positions only for the specific measurement time zones (TD2, TD3), as shown in FIG. 13, it is possible to suppress the reduction in the PRT to the minimum, as compared to the conventional method where the parallel tracking method is applied at all detection positions for all measurement time zones. Also, it is possible to prevent the simultaneous detection at the plurality of positions by widening the interval of the detection positions of the shear wave. In this case, it is possible to avoid a situation where a time zone for which the parallel tracking method is applied occurs. As described in the first illustrative embodiment, the interval of the detection positions may be manually changed by the operator through the input unit 6 or may be automatically set by the apparatus.

A measurement flow of the shear wave of the second illustrative embodiment is the same as the measurement flow of the first illustrative embodiment shown in FIG. 8. However, in steps S12, S22, S40 of FIG. 8, the time at which the measurement is over with the respective detection values is when the absolute value of the displacement amount is below the threshold TH. Also, in step S50, the shear wave is spectrum-analyzed to estimate the frequency characteristic of the shear wave velocity and the viscosity parameter such as the shear viscosity.

In a modified embodiment of the second illustrative embodiment, a measurement method of measuring the group velocity with the method of the first illustrative embodiment at first time and measuring the viscosity parameter at second time may be performed. In this case, the value displayed on the display unit 5 in step S60 is the viscosity parameter such as the shear viscosity, in addition to the values described in the first illustrative embodiment. Also, a graph showing a relation between the shear wave velocity and the frequency may be displayed. Also, when the parallel tracking method is applied, 'Parallel: ON' may be displayed on the display unit 5 in the display example of FIG. 9, and the operator can visually check the detection method of the shear wave.

Furthermore, as the value for evaluating the degree of reliability of the measurement value of the hardness information of the tissue in the living body, which is the subject, the degree of reliability may be determined from a correlation function of the waveforms of two or more shear waves detected at different positions, in addition to the standard deviation described in the first illustrative embodiment with reference to FIG. 9. When the shear wave propagates through an ideal homogeneous medium, the waveforms of the shear waves at the different detection positions are similar to each other. However, when two or more tissues exist and acoustic parameters of the tissues, for example, the shear wave velocity, the viscosity and the like are different in a region through which the shear wave propagates, the waveform similarity of the shear waves is lost as the shear wave propagates. The higher the similarity, the maximum value of the correlation function becomes larger and the variance value or standard value of the correlation function becomes smaller. Therefore, as the degree of reliability displayed on the display unit 5, the correlation function of the waveforms of the two or more shear waves, which is a value indicating a degree of similarity of the waveforms of two or more shear waves, may be used.

Figure 14A:
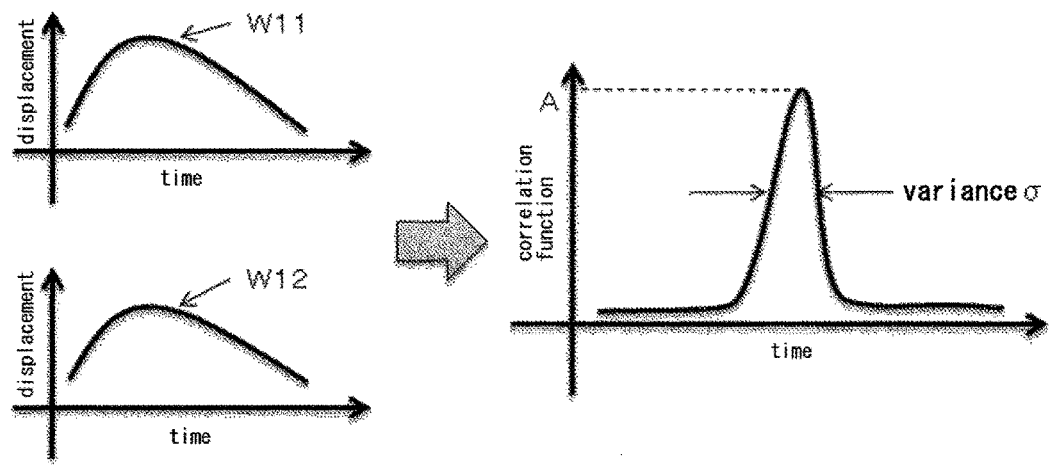
FIG. 14A illustrates an example of the correlation function of the shear wave in the second illustrative embodiment.
Figure 14B:
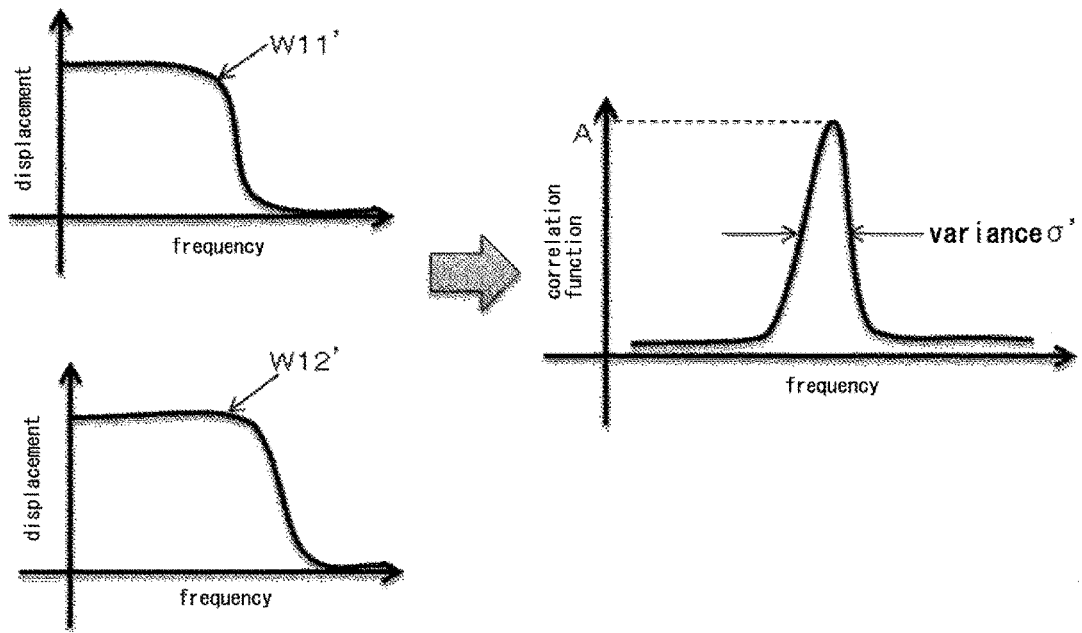
FIG. 14B illustrates an example of a correlation function of the shear wave in the second illustrative embodiment.

The correlation function is described with reference to FIGS. 14A and 14B. The correlation function can be calculated using temporal waveforms of two different shear waves or waveforms of spectrum values thereof. FIG. 14A illustrates a graph of a correlation function, which is calculated using temporal waveforms W11, W12 of the shear waves, and a maximum value A and a variance value σ of the correlation function. Also, FIG. 14B illustrates a graph of a correlation function, which is calculated using frequency spectra W11', W12' of the displacement of the shear waves, and a maximum value A' and a variance value σ' of the correlation function. The maximum value or variance value or both values are displayed on the display unit 5, so that the operator can evaluate the degree of reliability of the measurement result. As the waveform that is used for calculation of the correlation function, the waveforms of the particle velocity, the phase rotation amount, the phase, the acceleration and the like of the shear wave may be also used, in addition to the temporal waveform of the shear wave.

According to the ultrasonic diagnostic apparatus of the above-described second illustrative embodiment, it is possible to accomplish the effects capable of evaluating the frequency dependency of the shear wave and also evaluating the degree of reliability of the measurement result, in addition to the effects of the apparatus of the first illustrative embodiment.

Third Illustrative Embodiment

Hereafter, a third illustrative embodiment is described. The third illustrative embodiment is an illustrative embodiment of the ultrasonic diagnostic apparatus configured to detect hardness of the subject, considering a reflected wave of the shear wave, too. That is, in the third illustrative embodiment, the detection unit 20 of the ultrasonic diagnostic apparatus is an embodiment of the configuration of detecting a traveling wave or reflected wave of the shear wave. In the meantime, although the configuration of the ultrasonic diagnostic apparatus of the third illustrative embodiment is the same as the apparatus configuration of the first illustrative embodiment shown in FIG. 1, the detection unit 20 can detect a traveling wave or reflected wave of the shear wave. In the first and second illustrative embodiments, only one direction is considered as regards the propagation direction of the shear wave and the reflection of the shear wave is not considered. In the third illustrative embodiment, a measurement method relating to a case where the shear wave is reflected is described. Here, a case where only the peak value is detected is described. However, a case where the viscosity is measured can be also considered in the same manner.

Figure 15:
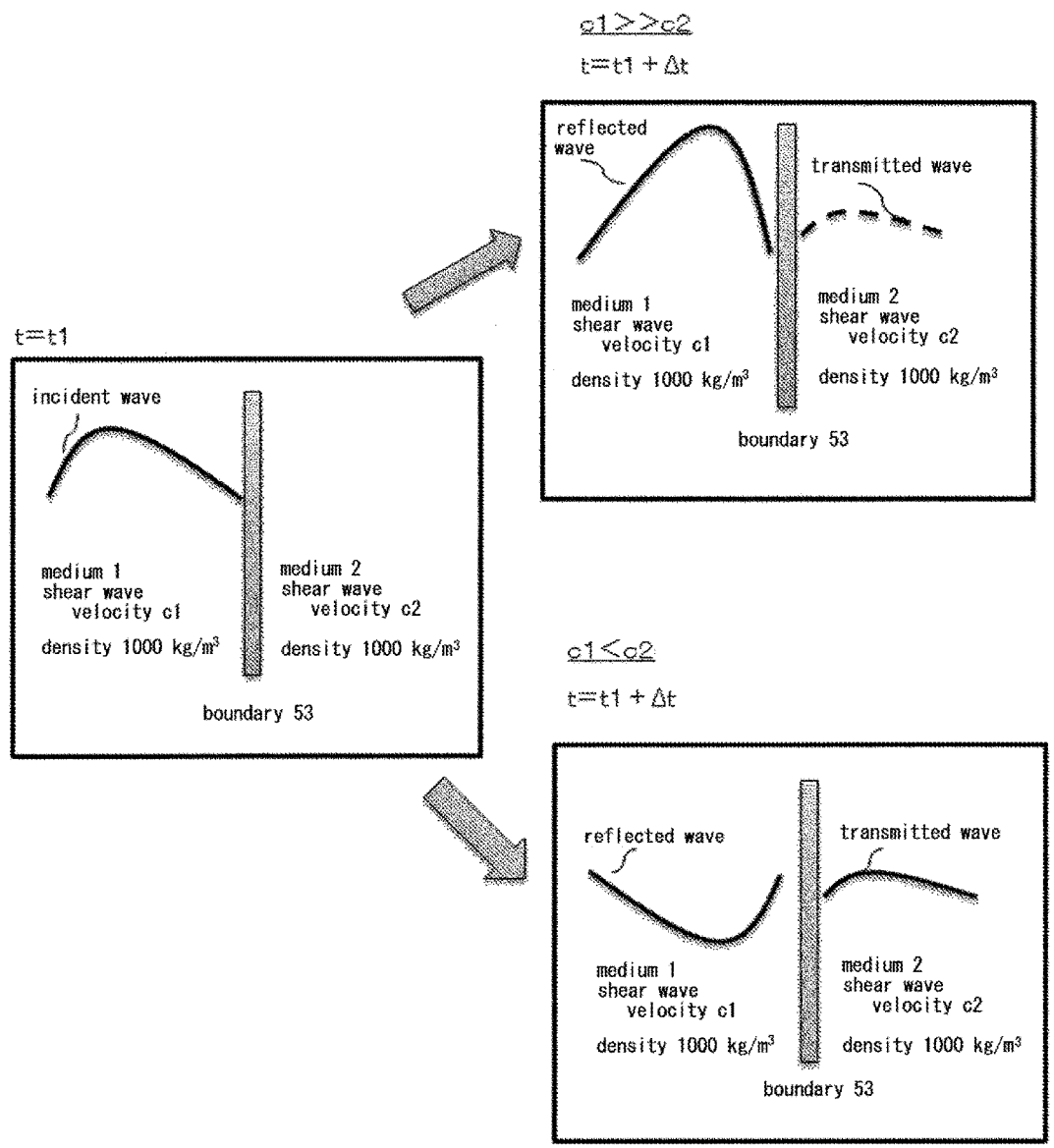
FIG. 15 illustrates a propagation direction of the shear wave when there is a boundary in a third illustrative embodiment.

First, the reflection of the shear wave is described with reference to FIG. 15. Here, it is assumed that the shear wave passes through a boundary of media 1, 2 in which shear wave velocities are different. FIG. 15 illustrates a vertical incidence, i.e., a case where a propagation direction of the shear wave is perpendicular to the boundary of the media. The shear wave before passing through a boundary 53 is referred to as an incident wave. The density of the media 1, 2 is about 1000 kg/m$^3$ when they are assumed as soft parts of the living body. At time t=t1, the shear wave is incident to the boundary. At time just after the incidence, i.e., at time t=t+Δt, the incident wave is divided into a transmitted wave and a reflected wave. Due to the shear wave velocities c1, c2 in the media 1, 2, an amplitude and a phase of the reflected wave of the shear wave are different.

When the shear wave velocity $c1$ in the medium 1 is sufficiently greater than the shear wave velocity $c2$ in the medium 2, i.e., when $c1 \gg c2$, a phase of the reflected wave is not reversed. Also, an amplitude value of the reflected wave is twice as large as that of the incident wave. When $c1 \gg c2$, an amplitude of the transmitted wave is sufficiently smaller, as compared to that of the reflected wave. On the other hand, when $c1 < c2$, the amplitude value of the reflected wave becomes smaller than that of the incident wave. Further, when $c1 < c2$, the phase of the reflected wave is reversed.

Figure 16:
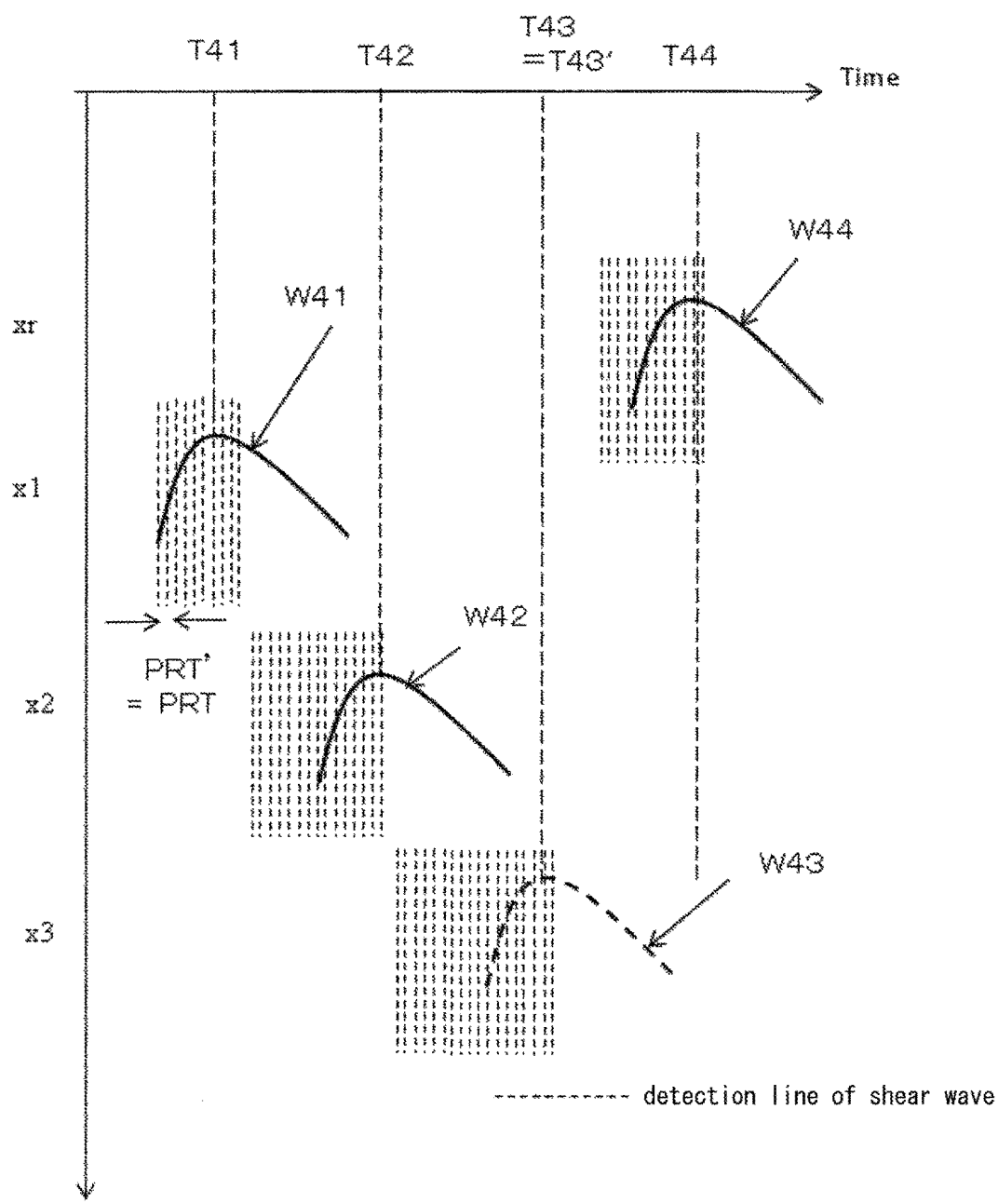
FIG. 16 illustrates a sequence of detection timings of the shear waves at the detection positions X1, X2, X3 in the third illustrative embodiment.

FIG. 16 illustrates a detection sequence of the reflected wave of the shear wave when $c1 \gg c2$. Here, it is assumed that the boundary exists between the detection positions $x2$, $x3$. In order to detect the reflected wave, a peak is detected at the detection position $x2$ and the peak detection of the shear wave starts at the detection position $x3$ starts. When there is no boundary, like the first and second illustrative embodiments, time T43 at which the shear wave peaks at the detection position $x3$ is predicted from the detection positions $x1$, $x2$ and peak time T41, T42 at the respective positions.

In this illustrative embodiment, the shear wave velocity at the detection position $x3$ is slower than the shear wave velocity at the detection position $x2$. For this reason, preferably, time obtained by adding $\Delta T$ to time T43 predicted from the detection positions $x1$, $x2$ and peak time T41, T42 at the respective positions is set, i.e., T43'=T43+$\Delta T$. $\Delta T$ is calculated by the central control unit 29 by reading a value of the shear wave velocity from the storage medium (not shown), depending on the measurement target. When the displacement does not exceed the threshold TH even at time T43', the detection position is changed to a position, for example, a position $xr$ located in an opposite direction to the propagation direction. At the detection position $xr$, the peak detection of the reflected wave starts. As the position at which the reflected wave is measured, a position $xr < x1$ is preferably set. More preferably, a position $xr = x2 - 2 \times (x2 - x1)$ is set. A sign of the peak of the shear wave detected at the detection position $xr$ is the same as those of the peaks detected at the detection positions $x1$, $x2$.

Figure 17:
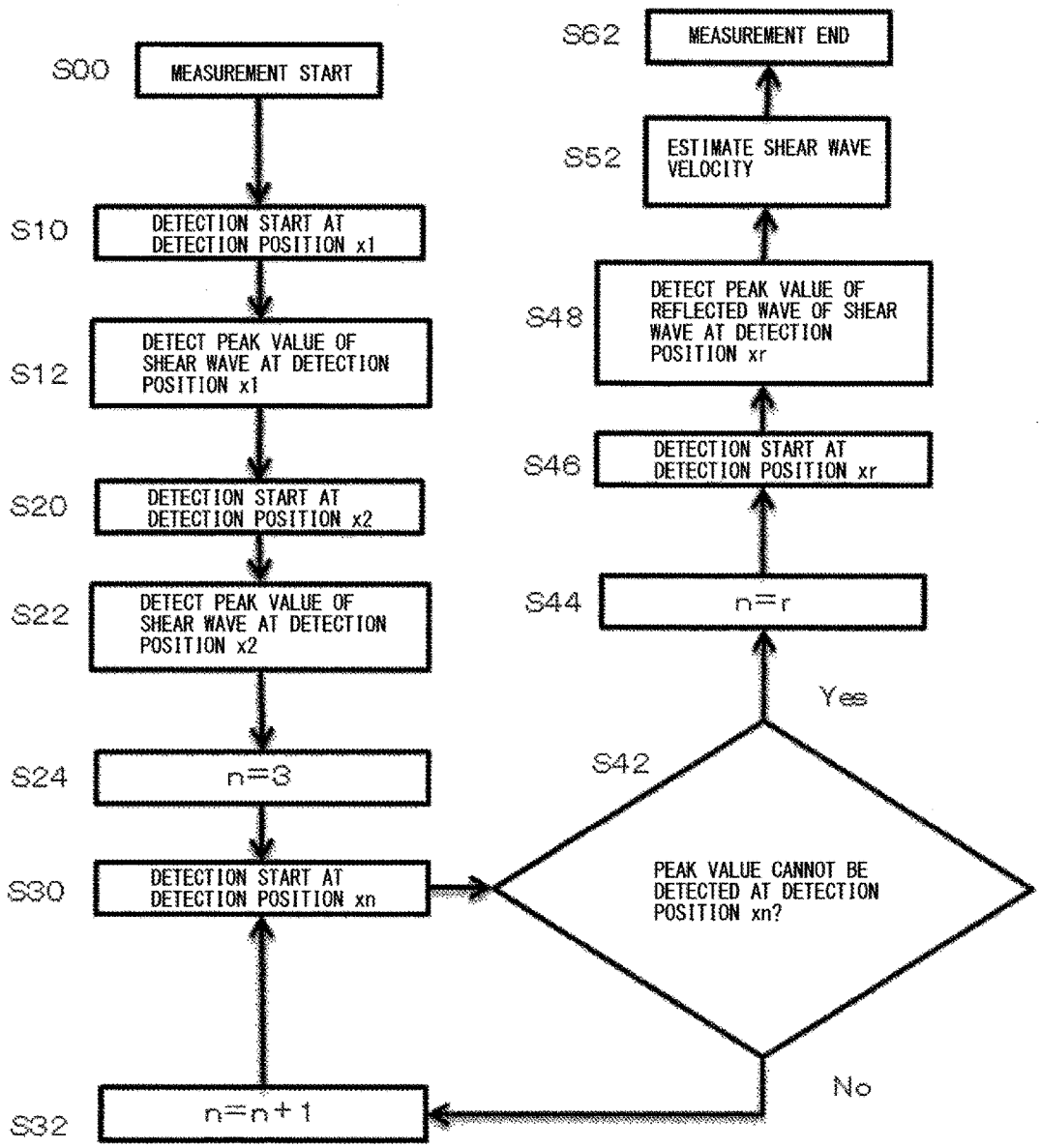
FIG. 17 is a flowchart showing a shear wave detection operation in the third illustrative embodiments.

A detection flow of the shear wave according to the third illustrative embodiment is described with reference to FIG. 17. Like the first and second illustrative embodiments, the sequence can be also implemented by the program processing of the CPU configuring the waveform analysis unit 26, the hardness information calculation unit 28 and the central control unit 29. Here, steps S42, S44, S46, S48, S52, S62 different from the detection flow of FIG. 8 described in the first illustrative embodiment are described.

In step S42, when a peak value cannot be detected at the detection position $xn$, the position is changed to a position $n$ (=r) in step S44. A position corresponding to r is output to the displacement detection transmission wave beam generation unit 22 directly from the waveform analysis unit 26 or through the central control unit 29. In the above example, the position $xr = x2 - 2 \times (x2 - x1)$. Regarding a value of $xr$, an optimal value is set depending on the detection position in step S30. In step S46, the detection of the reflected wave of the shear wave starts at the detection position $xr$.

In step S48, a peak value of the shear wave is detected at the detection position $xr$, and peak time T44 is output to the hardness information calculation unit 28. In step S52, a shear wave velocity, a coefficient of reflection and the like are calculated using the detection position, the peak value and the peak time.

In step S52, a reflection position is also estimated at the same time. The reflection position can be estimated using the detection positions $x2$, $xr$ and time T42, T44 at which the peak values are made at the corresponding positions. The calculation is performed in the hardness information calculation unit 28. When the measurement is over in step S62, a measurement result is displayed.

Figure 18:
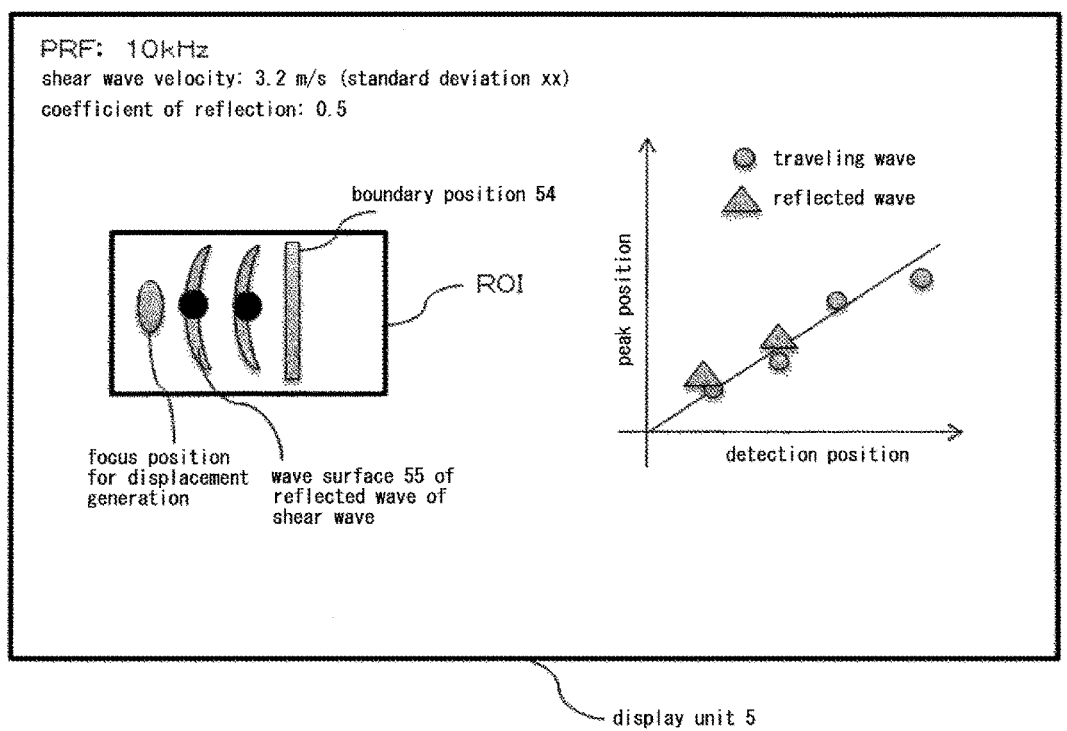
FIG. 18 illustrates an example of a display screen of a measurement result on the display unit 5 in the third illustrative embodiment.

FIG. 18 illustrates an example of the display screen of the display unit 5 in the third illustrative embodiment. The coefficient of reflection is displayed on the display unit 5, in addition to the shear wave velocity. Also, a wave surface 55 of the reflected wave of the shear wave and a boundary position 54 are displayed. Further, a graph showing positions of the traveling wave and the reflected wave may be displayed, as the peak position relative to the detection position. The operator can check whether the measurement is correctly performed while seeing the display unit 5. Also, the operator can specify a site of lesion and observe a symptom from the information of the boundary position, the coefficient of reflection and the like. When the reflected wave is not detected in step S48, an output value of the hardness information calculation unit 28 is the coefficient of reflection of 0, for example.

Here, a case where the measurement position of the reflected wave is one place is described. However, the number of the measurement positions may be two or more places. Also for the reflected wave, the entire wave surface may be measured to calculate the frequency characteristic and the viscosity parameter.

A detection method of the reflected wave is described when $c1 < c2$. In this case, since there is a transmitted wave as well as the reflected wave, it is not possible to evaluate whether the reflection is made, by using the threshold. In this case, it is determined whether there is a reflected wave from the damping characteristic of the displacement at the detection positions $x1$, $x2$, $x3$. In the below, the damping characteristic of the shear wave is described with reference to FIGS. 19A, 19B.

Figure 19A:
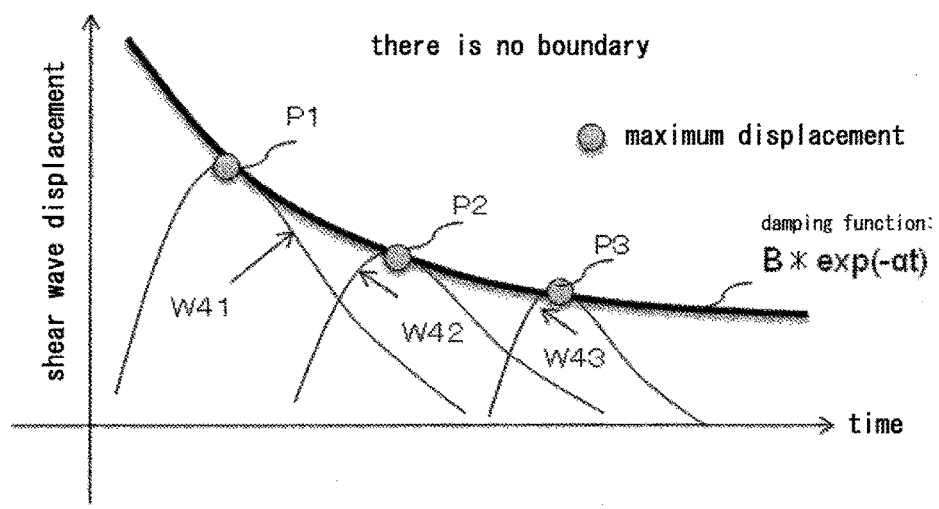
FIG. 19A illustrates an example (a case where there is no boundary) of a subtrahend characteristic of the displacement (amplitude) of the shear wave in the third illustrative embodiment.
Figure 19B:
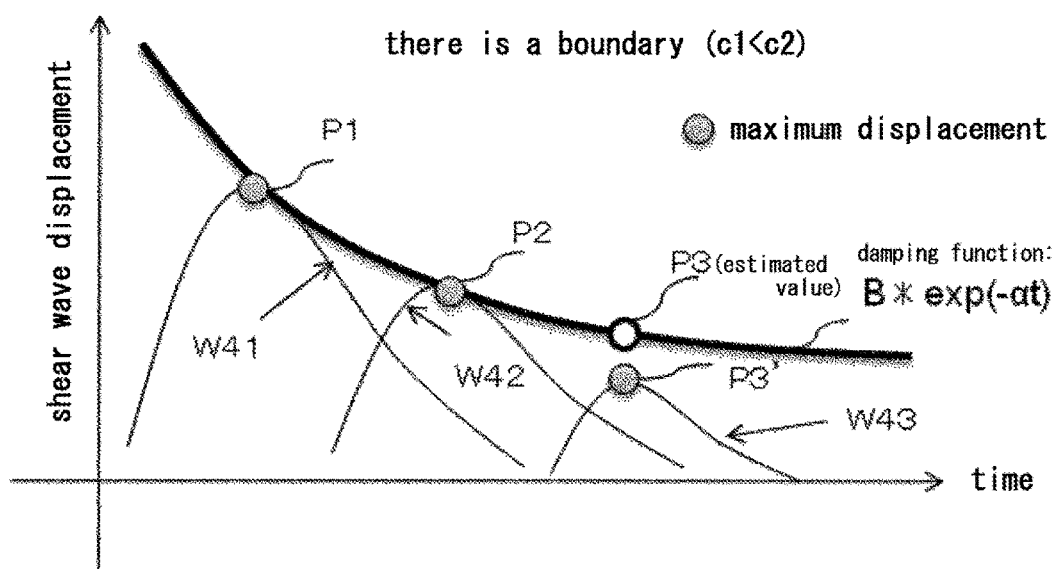
FIG. 19B illustrates another example (a case where there is a boundary) of the subtrahend characteristic of the amplitude of the shear wave in the third illustrative embodiment.

When there is no boundary, as shown in FIG. 19A, the maximum values P1, P2, P3 of the displacement of the shear waves at the respective detection positions and time at which the maximum values are made are expressed by a damping function. In the example of FIG. 19A, the maximum displacement P is expressed by $B \ast \exp(-\alpha t)$. $\alpha$ is a damping integer and t is time. Subsequently, a case where there is a boundary and $c1 < c2$ is described with reference to FIG. 19B. When the shear wave W43 is a displacement waveform after passing through the boundary, the maximum displacement P3' is a value smaller than a value when there is no boundary. When an error from the damping function, i.e., Pe $(=(P3-P3')/P3 \ast 100)$ is larger than a threshold, the shear wave W43 is regarded as a transmitted wave. As the threshold, 10% is used. For example, the damping function may be a function showing a general damping of a wave, such as Hankel function, in addition to the exponential function. A sign of the detected peak of the shear wave is the same as those of the peaks detected at the detection positions $x1$, $x2$.

In this illustrative embodiment, the operator can select whether or not to detect the reflected wave by using the input unit 6. Also, when the parallel tracking method described in the second illustrative embodiment is used, it is possible to detect both the transmitted wave and the reflected wave, irrespective of the coefficient of reflection. Further, this illustrative embodiment can be also applied to a general case where the propagation direction of the shear wave is not perpendicular to the boundary. According to the ultrasonic diagnostic apparatus of the above-described third illustrative embodiment, it is possible to accomplish the effect capable of evaluating the reflected wave of the shear wave, in addition to the effects of the apparatus of the first illustrative embodiment.

Fourth Illustrative Embodiment

Figure 20:
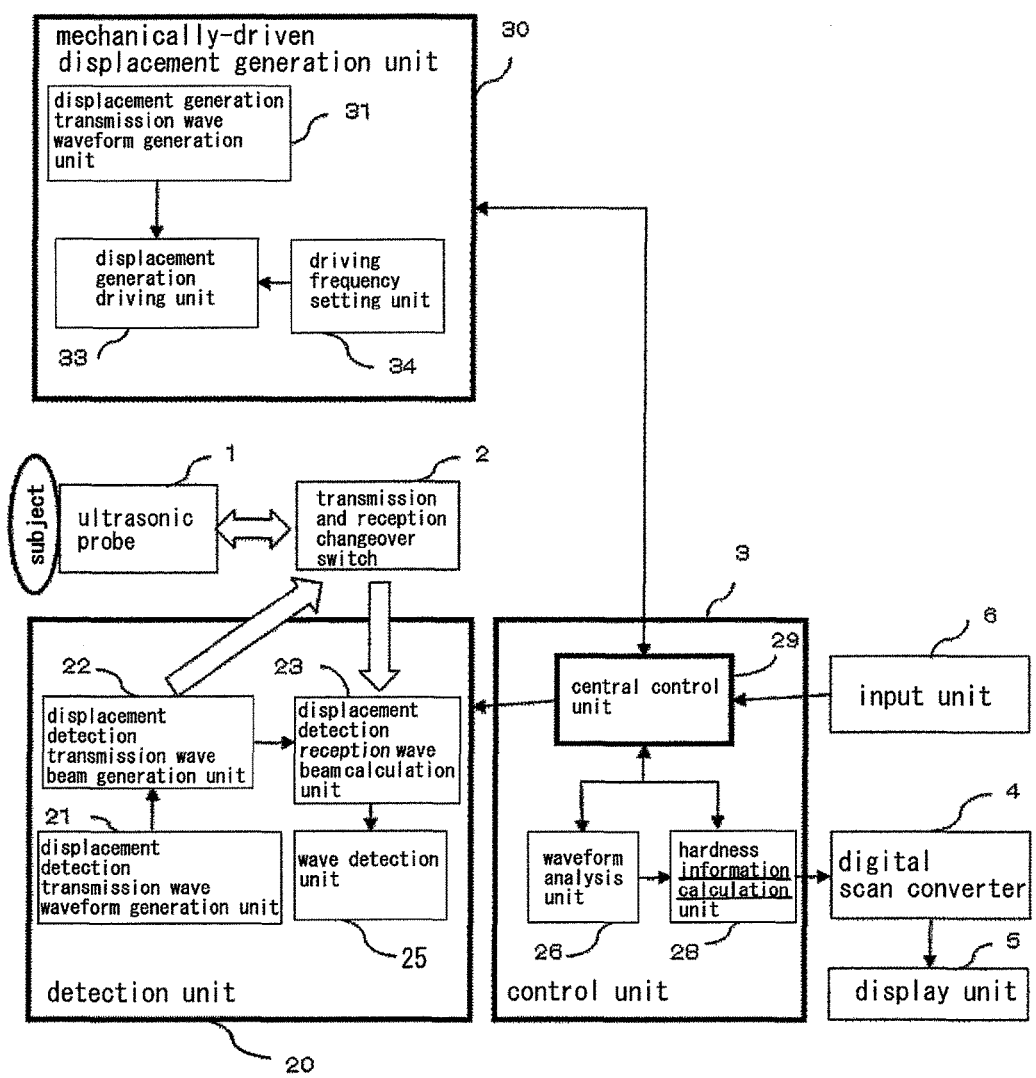
FIG. 20 is a block diagram showing an example of a system configuration of an ultrasonic diagnostic apparatus configured to generate a shear wave by using a mechanical driving source according to a fourth illustrative embodiment.

In the first to third illustrative embodiments, the displacement generation unit 10 is configured to emit the second ultrasonic beam, thereby displacing the subject. That is, the radiation pressure is generated by the focused beam of ultrasonic waves, so that the shear wave is generated. However, the well known methods such as a mechanical driving (a DC motor, a vibration pump and the like), a manual pressing, a pressing by an electric pulse, and the like may be also used, in addition to the radiation pressure. As a fourth illustrative embodiment, an illustrative embodiment of the ultrasonic diagnostic apparatus is described in which a mechanical driving configured to displace the subject by a mechanical vibration is used to touch and press the ultrasonic probe to a surface of the subject such as the living body. That is, a mechanically-driven displacement generation unit is an illustrative embodiment of the ultrasonic diagnostic apparatus configured to displace the subject by the mechanical driving. FIG. 20 illustrates a configuration example of the ultrasonic diagnostic apparatus configured to generate the shear wave by using the mechanical driving for measurement according to the fourth illustrative embodiment. Here, only differences from the FIG. 1 are described.

As can be clearly seen from FIG. 20, the displacement is generated from a mechanically-driven displacement generation unit 30, instead of the displacement generation unit 10. Also, a waveform used for the mechanical driving is generated by a displacement generation transmission wave waveform generation unit 31 and is then output to a displacement generation driving unit 33. Also, a driving frequency is set in a driving frequency setting unit 34. The displacement generation driving unit 33 is configured to drive an actuator (not shown) such as a motor. The actuator is touched to a body surface of the living body, thereby generating a displacement and a shear wave in the living body. A merit of using the mechanical driving, like this illustrative embodiment, is that since it is possible to ignore a temperature increase in the living body due to the mechanical driving, there are no limitations on the measurement time and the number of measurement times. Also, when the actuator is operated by a sinusoidal wave, it is possible to measure a viscosity parameter of a specific frequency component. However, the spatial resolution is lower, as compare to the configuration of the first to third illustrative embodiments where the radiation pressure is used. On the other hand, when the radiation pressure is used, the measurement should be performed at the measurement time and measurement interval at which the temperature increase in the living body does not exceed a limit value. However, the spatial resolution is higher because the focused beam can be irradiated to any position.

In the meantime, the present invention is not limited to the above-described illustrative embodiments and includes a variety of modified embodiments. For example, the above-described illustrative embodiments have been described in detail for better understandings and it is not construed to include all the described configurations. Also, a part of the configuration of any illustrative embodiment can be replaced with the configuration of the other illustrative embodiments, and the configuration of the other illustrative embodiments can be added to the configuration of any illustrative embodiment. Also, a part of the configuration of each illustrative embodiment can be added/deleted/replaced with the other configurations.

The above-described illustrative embodiments relate to the ON/OFF control of the transmission and reception, the processing method of the received signal, and the feedback of the transmission and reception control based on the results thereof. That is, when implementing the illustrative embodiments, a convex-type or sector-type probe may be used instead of the linear array-type probe, a two dimensional probe may be used and a type of a device to be used is not particularly limited inasmuch as it can transmit and receive the ultrasonic wave.

Also, regarding the respective configurations, functions, processing units and the like, the example of preparing the program for implementing parts or all thereof has been described. However, the parts or all thereof may be also implemented with hardware such as an integrated circuit.

REFERENCE SIGNS LIST

1: ultrasonic probe
2: transmission and reception changeover switch
3: control unit
4: digital scan converter
5: display unit
6: input unit
7: transmission wave beam for displacement generation
8: transmission wave beam for displacement detection
9: reception wave beam for displacement detection
10: displacement generation unit
11: displacement generation transmission wave waveform generation unit
12: focus position setting unit
13: displacement generation transmission wave beam generation unit
14: beam frequency setting unit
20: detection unit
21: displacement detection transmission wave waveform generation unit
22: displacement detection transmission wave beam generation unit
23: displacement detection reception wave beam calculation unit
25: wave detection unit
26: waveform analysis unit
28: hardness information calculation unit
29: central control unit
30: mechanically-driven displacement generation unit
31: displacement generation transmission wave waveform generation unit
33: displacement generation driving unit
34: driving frequency setting unit
50: approximation straight line
51: peak position
52: wave surface of shear wave
53: boundary
54: boundary position
55: wave surface of reflected wave of shear wave
100: element of ultrasonic probe

The invention claimed is:

1. An ultrasonic diagnostic apparatus, comprising:
   an ultrasonic probe;
   a displacement generator that displaces an inside of a subject, and generates a shear wave;
   a detector that transmits an ultrasonic beam from the ultrasonic probe to a first detection position at a high time resolution of the subject and receives a first reflection signal, detects a first displacement at the first detection position on a basis of the first reflection signal, transmits the ultrasonic beam to a second detection position farther than the first detection position on a basis of a position where the shear wave is generated, and receives a second reflection signal, and detects a second displacement at the second detection position on a basis of the second reflection signal; and
   a controller that calculates a velocity of the shear wave on a basis of the first displacement and the second displacement, and outputs hardness information of the subject,
   wherein the detector transmits the ultrasonic beam to the second detection position in response to receiving a signal, from the controller, which designates the second detection position,
   wherein the controller sends the signal, to the detector, which designates the second detection position in response to the controller calculating the first displacement at the first detection position and detecting a peak value of the first displacement by signal processing,
   wherein the controller dynamically switches the first detection position at which the first displacement is detected to the second detection position at which the second displacement is detected in response to an analysis result of a first time at which a displacement of tissue of the subject caused by the shear wave peaks at the first detection position,
   wherein the dynamically switching the first detection position at which the first displacement is detected to the second detection position at which the second displacement is detected includes the detector switching a detection time at which the ultrasonic beam for displacement detection is transmitted to each of the detection positions in response to the analysis result,
   wherein the controller switches a plurality of detection positions by utilizing an output of the detector,
   wherein the controller sets a detection time at the plurality of detection positions on the basis of the output of the detector,
   wherein the controller sets a second time at which the ultrasonic beam is transmitted to the second detection position dependent on the analysis result of the shear wave at the first detection position by the detector, and
   wherein a starting time of the transmitting the ultrasonic beam and the receiving first reflection signal to/from a detection position at or after an n-th detection position is determined by the controller by utilizing a peak detection estimation time estimated from a detection result of a peak of the shear wave detected at a detection position before the n-th detection position, wherein n>1.

2. The ultrasonic diagnostic apparatus of claim 1, wherein the detector alters the second detection position, in either cases of:
   wherein the peak value of the first displacement fails to be detected at the first detection position, or
   wherein the first displacement does not exceed a predetermined threshold.

3. The ultrasonic diagnostic apparatus of claim 1, wherein the controller calculates a group velocity of the shear wave on a basis of a peak value or a zero cross value of the shear wave, and outputs the hardness information on a basis of the group velocity.

4. The ultrasonic diagnostic apparatus of claim 1, wherein the controller calculates a phase velocity and a viscosity of the shear wave on a basis of spectrum values of the shear wave, and outputs the hardness information on a basis of the phase velocity and the viscosity.

5. The ultrasonic diagnostic apparatus of claim 1, wherein the controller sets an interval of detection positions.

6. The ultrasonic diagnostic apparatus of claim 1, further comprising an inputter that sets as the hardness information a group velocity of the shear wave or a phase velocity and a viscosity of the shear wave.

7. The ultrasonic diagnostic apparatus of claim 1, further comprising an inputter that sets an interval of detection positions.

8. The ultrasonic diagnostic apparatus of claim 1, further comprising a display that displays the hardness information.

9. The ultrasonic diagnostic apparatus of claim 8, wherein a standard deviation or a correlation function of waveforms of two or more shear waves is displayed on the display as a degree of reliability of the hardness information.

10. The ultrasonic diagnostic apparatus of claim 8, wherein the display displays a pulse repetition time (PRT) or pulse repetition frequency (PRF) of the ultrasonic beam.

11. The ultrasonic diagnostic apparatus of claim 1, wherein the detector detects a traveling wave or reflected wave of the shear wave.

12. The ultrasonic diagnostic apparatus of claim 1, wherein the displacement generator displaces the subject by a mechanical driving or emission of another ultrasonic beam.

13. A method of transmitting and receiving an ultrasonic beam, comprising:
   displacing an inside of a subject to generate a shear wave;
   transmitting an ultrasonic beam from an ultrasonic probe to a first detection position at a high time resolution of the subject and receiving a first reflection signal;
   detecting a first displacement at the first detection position on a basis of the first reflection signal;
   dynamically switching the first detection position to a second detection position of the subject to which the ultrasonic beam is transmitted to, subsequent to the first detection position, in response to an analysis result of a first time at which a displacement of tissue of the subject caused by the shear wave peaks at the first detection position, wherein the dynamically switching the first detection position at which the first displacement is detected to the second detection position at which the second displacement is detected includes switching a detection time at which the ultrasonic beam for displacement detection is transmitted to each of the detection positions in response to the analysis result;
   transmitting the ultrasonic beam to the second detection position and receiving a second reflection signal;
   detecting a second displacement at the second detection position on a basis of the second reflection signal; and
   calculating a velocity of the shear wave on a basis of the first displacement and the second displacement, thereby calculating hardness information of the subject;
   switching a plurality of detection positions by utilizing an output of a detector,
   setting a detection time at the plurality of detection positions by utilizing the output of the detector, setting a second time at which the ultrasonic beam is transmitted to the second detection position dependent on the analysis result of the shear wave at the first detection position, and determining a starting time of the transmitting the ultrasonic beam and the receiving first reflection signal to/from a detection position at or after an n-th detection position by utilizing a peak detection estimation time estimated from a detection result of a peak of the shear wave detected at a detection position before the n-th detection position, wherein n>1.

14. The ultrasonic diagnostic apparatus of claim 1, wherein the detector sets a third detection position farther than the second detection position on a basis of a position where the shear wave is generated on a basis of an amount of the second displacement detected at the second detection position.

15. The ultrasonic diagnostic apparatus of claim 14, wherein the detector sets the third detection position, in either case where a peak value of the second displacement is detected at the second detection position or where the amount of the second displacement exceeds a predetermined threshold.

16. The ultrasonic diagnostic apparatus of claim 14, wherein the detector sets another detection position farther than a previous detection position on a basis of a position where the shear wave is generated on a basis of an amount of a displacement detected by a previous detection.

17. The ultrasonic diagnostic apparatus of claim 1, wherein the detection of the peak value of the first displacement at the first detection position is by a High Pass Filter (HPF).

18. The ultrasonic diagnostic apparatus of claim 1, wherein the peak value is part of a temporal waveform of the shear wave.

19. The ultrasonic diagnostic apparatus of claim 1, wherein the designation of a detection position within an area of interest is along a detection line further into the area of interest.

20. An ultrasonic diagnostic apparatus, comprising:
an ultrasonic probe;
a displacement generator that displaces an inside of a subject, and generates a shear wave;
a detector that transmits an ultrasonic beam from the ultrasonic probe to a first detection position at a high time resolution of the subject and receives a first reflection signal, detects a first displacement at the first detection position on a basis of the first reflection signal, transmits the ultrasonic beam to a second detection position farther than the first detection position on a basis of a position where the shear wave is generated, and receives a second reflection signal, and detects a second displacement at the second detection position on a basis of the second reflection signal;
a controller that calculates a velocity of the shear wave on a basis of the first displacement and the second displacement, and outputs hardness information of the subject;
an inputter that sets as the hardness information a group velocity of the shear wave or a phase velocity and a viscosity of the shear wave; and
display that displays the hardness information, wherein a standard deviation or a correlation function of waveforms of two or more shear waves is displayed on the display as a degree of reliability of the hardness information, wherein the detector transmits the ultrasonic beam to the second detection position in response to receiving a signal, from the controller, which designates the second detection position, wherein the controller sends the signal, to the detector, which designates the second detection position in response to the controller calculating the first displacement at the first detection position and detecting a peak value of the first displacement by signal processing, wherein the controller dynamically switches the first detection position at which the first displacement is detected to the second detection position at which the second displacement is detected in response to an analysis result of a first time at which a displacement of tissue of the subject caused by the shear wave peaks at the first detection position, wherein the dynamically switching the first detection position at which the first displacement is detected to the second detection position at which the second displacement is detected includes the detector switching a detection time at which the ultrasonic beam for displacement detection is transmitted to each of the detection positions in response to the analysis result, wherein the controller switches a plurality of detection positions by utilizing an output of the detector, wherein the controller sets a detection time at the plurality of detection positions on the basis of the output of the detector, wherein the controller sets a second time at which the ultrasonic beam is transmitted to the second detection position dependent on the analysis result of the shear wave at the first detection position by the detector, wherein a starting time of the transmitting the ultrasonic beam and the receiving first reflection signal to/from a detection position at or after an n-th detection position is determined by the controller by utilizing a peak detection estimation time estimated from a detection result of a peak of the shear wave detected at a detection position before the n-th detection position, wherein n>1, wherein the detector alters the second detection position, in either cases of:

wherein the peak value of the first displacement fails to be detected at the first detection position, or wherein the first displacement does not exceed a predetermined threshold, wherein the controller calculates a phase velocity and a viscosity of the shear wave on a basis of spectrum values of the shear wave, and outputs the hardness information on a basis of the phase velocity and the viscosity, and wherein the designation of a detection position within an area of interest is along a detection line further into the area of interest.

* * * * *